US009435782B2

(12) United States Patent
Lenz et al.

(10) Patent No.: US 9,435,782 B2
(45) Date of Patent: Sep. 6, 2016

(54) LANDFILL GAS SURFACE MONITOR AND METHODS

(75) Inventors: Elmar H. Lenz, Westminster, CO (US); Ken W. Fossey, Westminster, CO (US)

(73) Assignee: Trimble Navigation Limited, Sunnyvale, CA (US)

( * ) Notice: Subject to any disclaimer, the term of this patent is extended or adjusted under 35 U.S.C. 154(b) by 862 days.

(21) Appl. No.: 13/353,038

(22) Filed: Jan. 18, 2012

(65) Prior Publication Data

US 2012/0191349 A1 Jul. 26, 2012

Related U.S. Application Data

(60) Provisional application No. 61/434,793, filed on Jan. 20, 2011.

(51) Int. Cl.
*G01N 33/00* (2006.01)
(52) U.S. Cl.
CPC .................................. *G01N 33/0075* (2013.01)
(58) Field of Classification Search
CPC ........... G01N 1/2273; G01N 21/3504; G01N 2030/025; G01N 30/68
USPC .......................................................... 702/24
See application file for complete search history.

(56) References Cited

U.S. PATENT DOCUMENTS

| 3,444,721 A * | 5/1969 | Hearn et al. ..................... 73/23.2 |
| 4,164,138 A * | 8/1979 | Burkhart ........................ 73/23.2 |
| 5,025,150 A * | 6/1991 | Oldham et al. ................ 250/253 |
| 5,682,145 A * | 10/1997 | Sweetman et al. ........... 340/632 |
| 6,664,533 B1 * | 12/2003 | van der Laan et al. ... 250/222.2 |
| 6,822,742 B1 * | 11/2004 | Kalayeh et al. ............... 356/437 |
| 7,588,726 B1 * | 9/2009 | Mouradian et al. ............ 422/83 |
| 2004/0263852 A1 * | 12/2004 | Degtiarev ............... G01M 3/38 356/437 |
| 2009/0090167 A1 * | 4/2009 | Groves ........................ 73/31.01 |
| 2009/0213380 A1 * | 8/2009 | Appel et al. .................. 356/437 |
| 2010/0171505 A1 * | 7/2010 | Norgaard et al. ............. 324/468 |
| 2010/0174508 A1 * | 7/2010 | Trowbridge et al. ......... 702/170 |
| 2010/0207751 A1 * | 8/2010 | Follmer et al. ............... 340/439 |
| 2011/0112787 A1 * | 5/2011 | Daw et al. ....................... 702/95 |
| 2012/0024042 A1 * | 2/2012 | Vass et al. ................... 73/23.34 |

\* cited by examiner

*Primary Examiner* — Gregory J Toatley
*Assistant Examiner* — Michael Dalbo
(74) *Attorney, Agent, or Firm* — Kilpatrick Townsend & Stockton LLP

(57) ABSTRACT

Embodiments of the invention provide systems, devices, and method for monitoring gas emissions within a geographic area. A method for monitoring gas emissions may include providing a gas-monitoring device configured to be moved within the geographic area. The method may also include determining geographic locations of the device as the device is moved within the geographic area, determining a quantity of one or more gases in the air as the device is moved within the geographic area, and associating the geographic locations with the quantity of gases to provide gas emissions data for the geographic area. The gas emissions data may be communicated to one or more external devices, sources, and/or systems for analysis, documentation, and/or compliance reporting.

30 Claims, 13 Drawing Sheets

LANDFILL GAS SURFACE MONITOR AND METHODS

CROSS-REFERENCES TO RELATED APPLICATIONS

This application claims priority to Provisional U.S. Patent Application No. 61/434,793 filed Jan. 20, 2011, entitled "Landfill Gas Surface Monitor and Methods." The entire disclosure of the aforementioned Provisional U.S. Patent Application is hereby incorporated by reference, for all purposes, as if fully set forth herein.

BACKGROUND OF THE INVENTION

Environmental sampling and data collection involves the collection of: discrete air, soil, surface water, and/or groundwater media samples. Samples are collected for analysis of physical and chemical properties that provide an indication on the environmental condition of the sampled media. Historically field sample analysis results were recorded by hand in a field notebook. The location of the collected sample was noted in the field book or marked on a printed map or aerial photograph.

A specific example involves landfills. In landfills, trash is compacted and then buried. In these anaerobic conditions, bacteria breaks down organic substances in the trash, thereby producing methane gas. The methane produced varies across and within landfills, depending on, for example, the type of trash, the moisture content, and the weather. While a fraction of this gas may be captured, e.g., by a gas recovery system, the rest is emitted into the atmosphere. Landfills are a primary source of emissions of methane to the atmosphere.

State and local governments (e.g., through the Clean Air Act) have set limits on the amount of methane that may be emitted by landfills. If the emissions exceed this amount, the landfill must take action (e.g., by collecting and combusting or utilizing methane) to reduce the emissions. Thus, there is a need for measuring methane gas emissions to assess possible environmental impact and predict or assess whether a landfill is in compliance with environmental regulations.

BRIEF SUMMARY OF THE INVENTION

Embodiments of the invention provide systems, methods, and devices for monitoring environmental conditions within a geographic area. For example, in one embodiment, the system and/or device may monitor gas emissions within a geographic area such as a landfill or along a pipeline (buried or above ground). In another embodiment, soil, water, air, and the like may be monitored for contamination, radiation levels, metal content, and the like.

In one aspect, embodiments of the invention provide a gas-monitoring device that is transportable by a user within a geographic area to monitor gas emissions within the geographic area (e.g., within a landfill or along a pipeline). The gas-monitoring device may include a computing component having a display for displaying information to the user and having one or more inputs for receiving input from the user. The gas-monitoring device may also include an emission-detecting component communicatively coupled with the computing component and configured to sample surrounding air as the gas-monitoring device is moved within the geographic area so as to monitor the gas emissions within the geographic area. The gas-monitoring device may further include a location detecting component communicatively coupled with the computing component and configured to determine a geographic location of the gas-monitoring device as the gas-monitoring device is moved within the geographic area. The computing component may be configured to associate the monitored gas emissions with corresponding geographic locations so as to provide gas emissions data for the geographic area.

The gas-monitoring device may additionally include an air sampling instrument having a gas inlet port fluidly coupled with the emission-detecting component so as to provide air to the emission-detecting component for sampling. The air sampling instrument may include a rod and a gas sampling tube that includes the gas inlet port. The rod may be configured to be grasped at a proximal end by a user and the tube may have a proximal end fluidly coupled with the emission-detecting component and a distal end coupled with the rod so that the gas inlet port is positioned near a distal end of the rod. The rod and the gas sampling tube may be coupled together such that when a distal end of the rod contacts the ground, the gas inlet port is positioned between about 1 inch and about 10 inches above the ground.

The gas-monitoring device may additionally include a communication component configured to communicate with an external device to transmit the gas emissions data to the external device. The computing component and the location detecting component may be components of a handheld device and the emission-detecting component may be a component of a separate device that wirelessly communicates the monitored gas emissions with the handheld device. The handheld device may include a trigger that is configured to initiate sampling of the surrounding air and/or determining of the geographic location upon activation. The emission-detecting component may include a flame ionization detection device. The emission-detecting component may also include a metal hydride storage matrix for storing hydrogen gas for the flame ionization detection device.

The gas-monitoring device may additionally include a storage medium for storing the gas emissions data for the geographic area and/or may include an analysis component configured to assess a quantity of one or more gases within the sampled air. The monitored geographic area may be a landfill. In another embodiment, the gas-monitoring device may be moved along a path within the geographic area where the path corresponds to a buried (or above ground) gas pipeline.

In another aspect, embodiments of the invention provide a system for monitoring gas emissions within a geographic area. The system may include a location detecting device configured to determine a geographic location of the location detecting device as the location detecting device is transported within the geographic area. The system may also include an emission-detecting device configured to sample surrounding air as the emission-detecting device is transported within the geographic area so as to detect a quantity of one or more gases. The system may further include a communication device configured to communicate (e.g., with an external device) information about the determined geographic locations and the air samples within the geographical area. Each of the air samples may be associated with a corresponding geographic location within the geographic area so as to provide gas emissions data for the geographic area.

The system may additionally include a computing device configured to associate the air samples with corresponding geographic locations to provide the described gas emissions data. The computing device may be located remotely from the geographic area and the computing device may communicate with the system's communication device to receive the information about the determined geographic locations and air samples within the geographical area. In some embodiments, the computing device, the location detecting device, and the communication device may be included in a single device separate from the emission-detecting device, and the emission-detecting device may wirelessly communicate various information with the communication device.

The system may additionally include an air sampling device having a gas sampling tube fluidly coupled with the emission-detecting device to provide air to the emission-detecting device for sampling. The air sampling device may include a rod configured to be grasped at a proximal end by a user. The gas sampling tube may be coupled with a distal end of the rod so that a gas inlet port of the gas sampling tube is positioned near the distal end of the rod. The emission-detecting device may include a flame ionization detection device and a metal hydride storage matrix for storing hydrogen gas for the flame ionization detection device.

In another aspect, embodiments of the invention may provide a method for monitoring gas emissions within a geographic area. The method may include providing a gas-monitoring device configured to be transported within the geographic area to monitor gas emissions. The method may also include determining with a location detecting component of the gas-monitoring device, geographic locations of the gas-monitoring device within the geographic area as the gas-monitoring device is moved within the geographic area. The method may further include determining with an emission-detecting component of the gas-monitoring device, a quantity of one or more gases in the air for each geographic location as the gas-monitoring device is moved within the geographic area. The method may additionally include associating with a computing component of the gas-monitoring device, the geographic locations with the quantity of one or more gases so as to provide gas emissions data for each geographic location where measurements are taken. The method may additionally include communicating with a communication component of the gas-monitoring device, the gas emissions data to one or more external devices.

In one embodiment, the emission-detecting component may be calibrated, which may include: determining that a reading of the emission-detecting component is within a defined tolerance when subjected to zero air and determining that one or more of the following is within a defined tolerance when subjected to a calibration gas: an accuracy of the emission-detecting component; a precision of the emission-detecting component; or a response time of the emission-detecting component.

In one embodiment, the method may additionally include determining one or more background air sampling conditions of the geographic area where the background air sampling conditions include an upwind condition and/or a downwind condition. The method may additionally include storing the one or more background air sampling conditions of the geographic area on a storage medium of the gas monitoring device. The method may additionally include communicating the one or more background air sampling conditions with the gas emissions data to the external device.

In one embodiment, the method may additionally include displaying a map of the geographic area on a display device of the gas emissions device, plotting a path within the geographic area along which the gas emissions device is to be transported, and/or displaying a data point for each geographic location where measurements are taken. The path along which the gas emissions device is to be transported may be received from an external device.

The method may additionally include alerting a user when the quantity of the one or more gases in the air exceeds a defined amount. The method may additionally include re-sampling an identified geographic location within the geographic area when the quantity of the one or more gases of the identified geographic location exceeds a defined amount. The geographic location may be identified by the computing component of the gas-monitoring device.

In one embodiment, communicating the gas emissions data to one or more external devices may include transmitting the gas emissions data to an owner, person, or agency responsible for the geographic location. In one embodiment, the gas-monitoring device may activate the determining a quantity of one or more gases process by determining: that the gas-monitoring device is located at a defined gas monitoring position, that a defined amount of time has passed since a previous air sampling, and/or that the gas-monitoring device has crossed a defined boundary of a trajectory along which the gas-monitoring device is moved.

The method may additionally include moving the gas-monitoring device along a path within the geographic area where the path corresponds to a buried gas pipeline and/or the geographic area corresponds to a landfill

BRIEF DESCRIPTION OF THE DRAWINGS

The present invention is described in conjunction with the appended figures.

Figure 1:
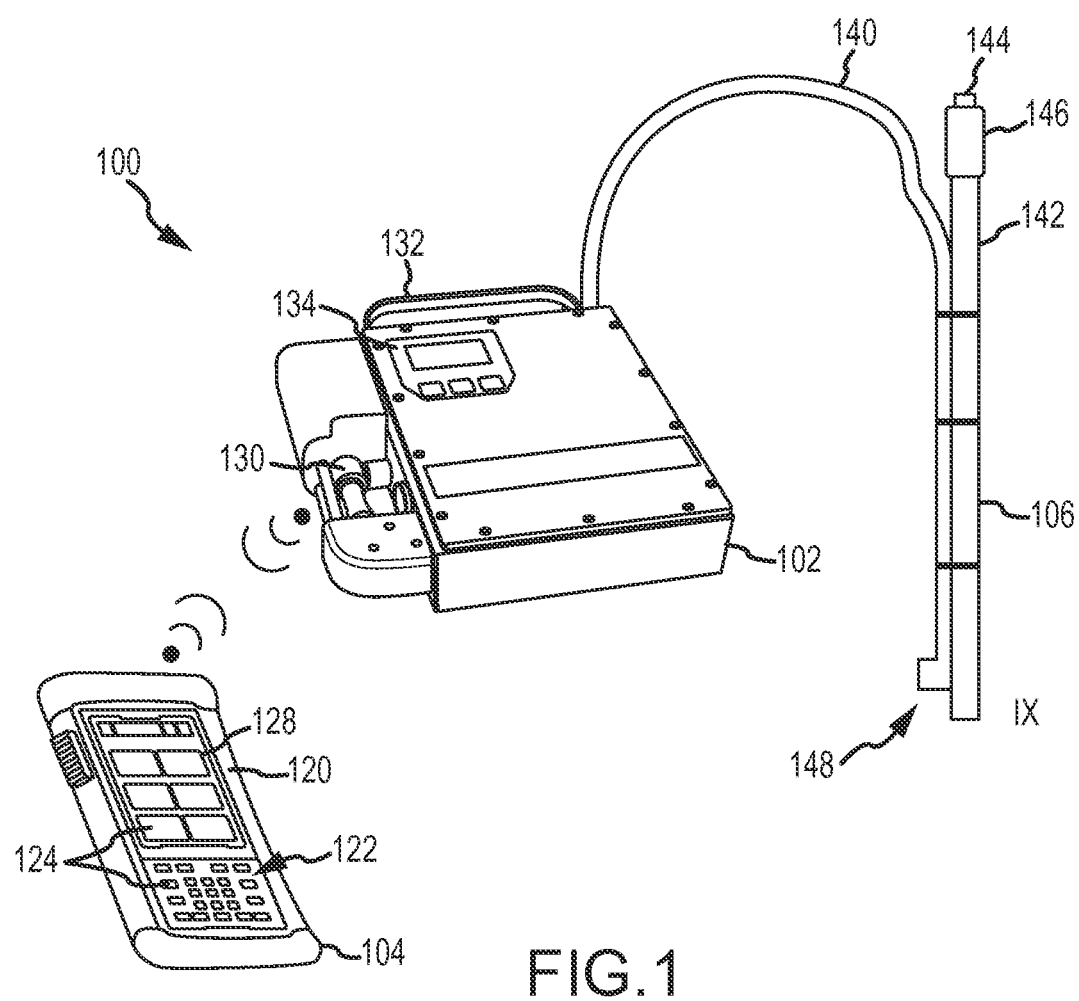
FIG. 1 illustrates a system for monitoring gas emissions according to an embodiment of the invention.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc.

The description herein uses the terms "zero air" and "calibration gas" to describe a process of calibrating the gas-monitoring device. The term zero air may refer to atmospheric air that is purified to contain less than 0.1 parts per million (ppm) total hydrocarbons. The term calibration gas may refer to a gas having a defined amount and/or concentration of hydrocarbons that is used to calibrate the gas-monitoring device, such as by measuring the precision, accuracy, and/or responsiveness of an air sample analysis component of the gas-monitoring device. In some embodiments, the calibration gas may use 500 ppm of a specific gas, such as methane, hexane, and/or the like. The description also uses the terms "upwind" and "downwind" to describe certain background conditions. The term upwind may refer to the direction the wind is coming from relative to a user of the gas-monitoring device and the term downwind may refer to the direction the wind is traveling.

Embodiments of the invention provide a portable environmental sampling device that can be moved within a geographic area to sample air, soil, groundwater, and the like to detect various conditions in the air, soil, and/or groundwater. Examples of the sampling that can be performed include monitoring surrounding air for gas emissions, using x-ray diffraction to monitor and/or measure metals within the ground, monitoring and/or measuring radiation levels to determine ground radiation, and the like. For convenience, the description herein will mainly describe monitoring air samples to determine gas emissions, although it should be realized that soil and/or ground water likewise may be monitored to determine various other environmental conditions. Thus description herein is, thus, not limited to applications involving monitoring air samples only, but is also meant to include monitoring soil and/or groundwater to determine various environmental conditions.

The portability of the sampling device allows for environmental samples (e.g., air, soil, and/or groundwater) to be analyzed for their physical or chemical properties in the field right where the samples are collected and the results may be immediately available to the sampler. The immediate analysis of environmental samples has a benefit of providing real time feedback on the environmental condition of the media being monitored. These real time results can then be used to identify areas of interest and guide the environmental investigation and additional sample collection. The portable sampling device provides an improved approach by providing direct recording of monitored data from environmental instrumentation on a portable device. This replaces the hand entry of monitored data in a field notebook and any associated errors. The portable sampling device also provides latitude and longitude position of the sample locations. The portable sampling device may further automatically log the environmental data and append the GPS location data to the monitored data, eliminating the need to hand record the monitored data and to manually estimate and mark the sample location on a map or aerial photograph. The portable sampling device can also provide a field sampler with a geo-referenced site map and current location so that the field worker can locate the position from which samples are being collected.

Embodiments of the invention described herein provide gas-monitoring devices and methods for monitoring or sampling air to detect the presence, quantity, and/or concentration of one or more specified gases in the sampled air. Embodiments of the invention may provide one or more advantages over other gas monitoring devices and techniques. For example, the described gas-monitoring devices and methods may provide monitoring assessments in real-time. This may improve monitoring efficacy (e.g., by encouraging a surveyor to follow-up with concerning areas) and may improve safety (e.g., by alerting the supervisor and/or owner of dangerous gas levels). Other possibly advantages may include documenting a location or locations of landfill gas surface sampling in one or more sample grids, documenting that a sampling traverse in a sample grid was conducted per defined or specified regulatory requirements, accurately identifying and/or documenting a location of instantaneous exceedance (i.e., exceedance beyond a defined amount), providing a sampling technician with feedback in the field that they are adequately following a sampling plan and planned traverse, providing a sampling technician with an integrated reading for a sample grid in real time to assist in identifying areas of increased landfill gas concentrations within the sample grid, providing an immediate integrated sample result at the end of grid sampling, precisely identifying a location or locations of instantaneous exceedance within a grid, providing the exact location of gas emission exceedance to an operator conducting corrective action to reduce gas emission levels, providing the exact location or locations of the exceedance to a sampling technician who is re-sampling (or going to resample) an area after a corrective action is implemented, automating the gathering of data and output to tables for inclusion in an annual compliance report, automating the transfer of field monitoring reading and positioning location to an owner's compliance management system, and the like.

Some embodiments relate to a portable gas-monitoring device. The portable gas-monitoring device may regularly or continuously detect an amount and/or concentration of a gas (e.g., methane) and associate the detected concentration with position information. This information may be stored in the device or transmitted to a central system such that, e.g., the data may be recalled or reported at a later time or transmitted to an owner of a monitored site for subsequent evaluation and/or transmittal to a regulatory agency. A concentration map may be generated based at least partly on the detected concentrations and the position information and displayed or stored on the gas-monitoring device or the central system. The map may indicate locations where the detected concentration or where an average concentration exceeded a threshold, and it may also indicate a current position of the gas-monitoring device.

Because the gas emissions may vary across a given landfill, the emissions are frequently measured at a plurality of locations within the landfill. A surveyor with a gas-monitoring device may make a defined trajectory across a landfill or make one or more measurements within various regions of the landfill. In some instances, an average emission measurement is calculated for each of a plurality of regions. Thus, for example, the surveyor may collect a fixed number of measurements within the region or collect measurements for a fixed time period in order to provide measurements for an average calculation. A surveyor may return to particular (e.g., high-emission) locations within the landfills at a later time to measure updated emission concentrations, such that it can be determined whether intermediate emission-reducing measures were effective.

One method of detecting gas (e.g., methane) emissions comprises measuring gas emissions at a plurality of locations, determining and noting location information (e.g., longitude and latitude coordinates) at each location, and recording (e.g., by hand) the measured emissions and location information. This method may be time-consuming and prone to errors. Additionally, if a surveyor detects a high emission within part of a region, he may wish or need to collect more measurements around that region. However, if he was collecting samples within the region during a set time period, immediately finely surveying the sub-region could bias the measurements to be used for an averaging calculation. Even attempting to pause the clock while the fine-scale surveying was performed could introduce complexities that may lead to sampling errors and inefficiencies. Further, it may be difficult and time-consuming for a surveyor to return to a particular (e.g., high-emission) location to subsequently repeat the monitoring. In some embodiments, a more technological approach may be employed. For example, a monitoring device may automatically detect locations of emission measurements and store and/or transmit the emission measurements and detected locations.

A gas-monitoring device may include an emission-detecting component. The emission-detecting component may include, for example, an air import port configured to receive a sample of the surrounding air. The component may include an analysis component configured to assess the components of the sample. For example, the analysis component may include a gas-chromatography subcomponent, a mass-spectroscopy subcomponent, an absorption spectrometer, a photoionization detector, a (e.g., thermal, electrolytic conductivity detector, and/or flame-ionization detector). The component may include a hydrogen tank.

In some embodiments, the gas-monitoring device does not receive surrounding air through an input port. Instead, an air-monitoring assessment may be conducted remotely outside of the device. For example, the device may emit a heat or optical source that would interact with methane gas if it were present, e.g., in a concentration-dependent manner. An analysis component (e.g., a light or heat detector) may assess any such interaction.

The device may include a processor that may receive results from the analysis component. The processor may calculate a predicted gas concentration based on the received results. The processor may also identify error bars or confidence intervals and/or relate the calculated concentration to a threshold (e.g., by noting calculated concentrations exceeding the threshold). One or more summary variables may be determined by the processor. Examples of summary variables may include an overall compliance or non-compliance variable, a number of over-threshold emission locations, and/or an average emission measurement.

The gas-monitoring device may include a trigger. The device may be configured such that a gas-monitoring measurement is taken when the trigger is activated (e.g., by a user pressing a trigger button). Prolonged trigger activation may cause the device to continually or regularly conduct measurements. In some instances, a single trigger activation may cause the device to continually or regularly conduct measurements. The device may also include one or more mode-changing components (e.g., depressable button or touch-screen activated button), which may allow a user to elect that the device collect measurements in a desired mode. The modes may include monitoring modes or functional modes. Examples of monitoring modes include continuous monitoring, regular monitoring (e.g., every five seconds), continuous time-averaged monitoring (e.g., repeatedly averaging overlapping or non-overlapping periods of data), and/or discrete monitoring. Examples of functional modes include an initial measurement mode, during which a user is to semi-uniformly traverse across an entire region or site; a follow-up mode, during which a user is to obtain measurements within a particular area (e.g., of concern) within a region or within a site; and a subsequent-visit mode, during which a user is to return to previously identified locations to repeat emission measurements.

The gas-monitoring device may include a location detector. The location detector may include, for example, a global positioning system based on signals received from a plurality of satellites. The location detector may include an accelerometer or speedometer. The location detector may include a signal transmitter and signal receiver. For example, the device may emit radio waves. Towers within a network may receive the signal and transmit its own response signals or reflect the signals. Position information may be determined by assessing the time difference between the signal emission and receipt from one or more towers and/or assessing signals properties indicative of the tower that received the emitted signals.

The location detector may determine location information. The location information may include global coordinates (i.e., longitude and latitude). The location information may include relative coordinates (e.g., with respect to a corner or center of a landfill or a specific location or region). The location information may include a distance from a specific location or region, such as a location or region with previous emission measurements exceeding a threshold. In some embodiments, location information is continuously or regularly detected. In some instances, location information is detected each time emission data is gathered.

The gas-monitoring device may include a storage unit. The storage unit may be configured to store date and time information, site-specific information (e.g., a landfill name, an owner's name, or a landfill's address), summary variables, location information (e.g., relating to locations of specific emission measurements), emission measurements and/or variables relating to emission measurements (e.g., binary outputs indicating whether emission measurements exceed a threshold or average emission measurements). Related data and information may be associated with each other in the storage unit. For example, emission data gathered at a particular location at a particular time may be associated with the appropriate location and time information. The storage unit may or may not be removable from the device. For example, the storage unit may include a solid-state drive, a spinning-disc drive, SID card, a compact disc, a DVD, or USB drive.

The gas-monitoring device may include an output component. The output component may include, for example, a port configured to receive a cord or cable. The output component may include a wireless card or Bluetooth technology. The device may send data through the output component to a network, such as an intranet or the world-wide web. The data may include a map, location information, emission measurements, variables relating to emission measurements, summary variables, site-specific information and/or date and time information. The device may continuously, regularly or discreetly transmit data via the output component. In one instance, the device may output the data after all measurements have been collected on a specific area (e.g., a landfill) on a specific day.

The gas-monitoring device may include a data input component. The data input component may include a wireless card, Bluetooth technology or a port configured to receive a cord or cable. The device may receive data through data input component from a network, such as an intranet or the world-wide web. The data may include a map, location information, emission measurements, variables relating to emission measurements, summary variables, site-specific information and/or date and time information. The device may continuously, regularly or discreetly receive data via the data input component. In one instance, the device may receive the data before collecting measurements on a specific area (e.g., a landfill) on a specific day.

The gas-monitoring device may include a display. The display may show location information, emission measurements, variables relating to emission measurements, summary variables, site-specific information and/or date and time information. The displayed data may be current and/or past data. The display may show a map. The display may show surveying instructions, such as a trajectory that the surveyor is supposed to follow or indications as to when the surveyor should stop and/or take a measurement.

A map may show locations at which specific or summary emission measurements are to be taken or were previously taken. For example, in embodiments for which the device continuously or regularly monitors emissions, the map may show a trajectory that the surveyor is to follow or previously followed, which will also be indicative of locations where measurements are to be taken or where measurements were taken. In embodiments for which discrete measurements are to be taken, the map may show indicators at locations where the surveyor should initiate a measurement. The map may show previous discrete or summary emission measurements. Such measurements may comprise, for example, numeric values, text descriptions, symbols, and/or color indicators. For example, a symbol may be present at any location or region with a measurement or summary variable exceeding a threshold. As another example, a symbol may be present at every location or region but may have a shape or color indicative of the emission measurement or summary variable.

The map may show data from a previous monitoring session and/or from the current session. The map may show an indication (e.g., a symbol) of where the device or surveyor is currently located. The map may show site-specific features (e.g., a perimeter or grid regions). The gas-monitoring device may include power supply, such as a battery In one embodiment, a method for monitoring a gas emission is provided using a gas-monitoring device. The gas-monitoring device may be calibrated. The calibration may include measuring zero air, and determining whether the reading is within a tolerance. If it is, the device's accuracy and/or precision may be calibrated using a calibration gas (e.g., a 500 ppm methane gas). The devise's response time may also be calibrated.

Site-specific information may be received, e.g., by a person inputting (e.g., typing) information to the gas-monitoring device, from an external storage device, or from a system receiving and sending data to and from the device. The site-specific information may include, for example, a name of a property, a location of a property, a name of an owner of a property, and boundaries of a property. In some instances, the site-specific information includes a map.

Calibration accuracy, precision and response time may be compared to tolerance ranges. If one or more of these values are outside the tolerance ranges, it may be recommended to at least temporarily refrain from collecting monitoring data.

Site background readings may be obtained. The background readings may include, for example, upwind and downwind background readings. If background conditions change during a monitoring process, site background readings may be repeated.

A monitoring trajectory can be determined, e.g., by a processor of a device or by receiving the trajectory from a connected system or from an external storage device. The monitoring trajectory may be determined based on applicable regulations, e.g., indicating how frequently, where, and for how long emission measurements must be taken. In some instances, determining a monitoring trajectory comprises dividing a property into a plurality of grid regions and determining a trajectory within each grid region. The area and location of the grid region may again be chosen to comply with applicable regulations. The monitoring trajectory may indicate the path a surveyor is to follow, the speed that he is to walk and/or locations that he is to collect discrete emission measurements.

An activation may be detected. In one instance, the device includes a component configured to let a user expressly activate the device. Such a component may comprise a button. In one instance, the device detects the device moving along a particular trajectory or crossing a particular boundary and thereby activates the device.

A monitoring mode may be chosen. Monitoring modes may include, for example, discrete, regular or continuous monitoring modes. In some instances, a default mode (e.g., a continuous mode) is set. In some instances, the user cannot switch modes. A functional mode may be chosen. Functional modes may include, for example, an initial measurement mode, during which a user is to semi-uniformly traverse across an entire region or site; a follow-up mode, during which a user is to obtain measurements within a particular area (e.g., of concern) within a region or within a site; or a subsequent-visit mode, during which a user is to return to previously identified locations to repeat emission measurements.

An emission level may be measured, e.g., by measuring a concentration of a gas. The gas may comprise methane. The emission level may be measured using, for example, gas chromatography, mass spectroscopy, absorption spectrometry, photoionization detection, conductivity detection, and/ or flame-ionization detection. The emission level may be measured at separate time points (e.g., following a trigger activation), at regular time intervals or continuously. For example, the emission level may be measured every approximately 0.5 seconds.

One or more variables relating to emission measurements may be calculated. The variables may include, for example, a maximum, minimum, median, mean or mode emission, predicted error or confidence intervals. In one instance, average emission levels are calculated, wherein every approximately 5-6 seconds an average is calculated based on all measurements obtained during that time period.

In some instances, emission-level measuring techniques are changed upon a notification of a new monitoring mode or of a new functional mode. For example, an initial measurement mode may initially be selected. In some instances, the remote device would then measure emission concentrations at regular intervals (e.g., 0.5 seconds), as a surveyor walked along a defined trajectory. The regular readings may be consolidated to averages. For example, an average could be calculated by averaging all readings occurring within a five-second interval. This average could be associated with an average location. However, if an average emission level exceeded a threshold, a surveyor may change the mode to a follow-up mode, such that he could divert from the defined trajectory and more thoroughly explore an area surrounding the concerning emission level. In such a case, a timer associated with the trajectory may be paused and the data may be stored separately from the data obtained before the mode change. The surveyor may, for example, revert back to his initial path by again changing the functional mode.

Location information may be determined. The location information may comprise, for example, a predicted location (e.g., longitude and latitude coordinates) of the mobile device. The location information may be determined using, for example, a global positioning system. The location information may be associated with the emission-level measurements. For example, each emission-level measurement may be accompanied by location information indicating where the device was when that measurement was obtained. Each emission-level measurement may also be accompanied by time and/or date information indicating when that measurement was obtained.

Data may be stored and/or transmitted. The data may include, for example, emission-level measurements, location information, time and/or date information, and/or site-specific information. The data may be formatted into a spreadsheet. The data may be stored in a local or external device. The data may be transmitted (e.g., wirelessly or via a physical connection) to a central system. The central system may include a computer with a processor and software with instructions to receive the data; process the received data; and/or transmit at least part of the original data or the processed data back to the device before a subsequent monitoring session. The central system may be a system maintained by an owner, agency, or person responsible for the monitored site. Upon review of the information, the owner, agency, or person responsible for the monitored site may transmit the data to a regulatory agency for reporting and/or compliance purposes.

A map may be generated. The map may either be generated using a processor of the device or a processor of the central system. If the map is generated at the central system, the map may be sent to the device. In some instances, map generation begins with a map showing a general features of a property (e.g., a perimeter of the property or identifications of portion of the property devoted to different uses). The map may comprise a satellite map or an aerial-photo image map. The map may show features as described above (e.g., a surveyor's trajectory, emission information, a surveyor's location, and locations with emission measurements exceeding a threshold). The map may be displayed on the device.

Subsequent measurements may be obtained at positions of interest. Using, for example, map symbols may be shown indicating prior threshold-exceeding measurements. A surveyor could locate the position of interest by noting an indication on the map corresponding to his location and noting the depicted position of interest. Additionally, the device may display a distance from the position of interest or instructions about how to get there. The survey may be alerted when he has reached the position of interest. He may set a functional mode to a subsequent-visit mode and collect new data. The new data may again be stored and/or transmitted as described above.

Devices and methods herein can eliminate the need to record by hand emission levels and location information associated with the levels. Thus, emissions of an area may be monitored more quickly and with fewer errors. Because monitoring may thus be faster, more thorough sampling may also be possible. Not only does it reduce the possibility of inadvertent errors, but devices and systems may also make intentional mis-reportings more difficult. Any intentional or unintentional errors would be logged, such that curious readings could be explained. Thus, regulators may be more confident that favorable reportings are accurate.

Additionally, a surveyor can change his mode of surveying from a first-level initial scan to a more detailed scan around a region of interest. This allows him to study the region of interest while he is already there, eliminating the need to attempt to relocate the place, and it maintains the validity of the previously recorded data.

Referring now to FIG. 1, illustrated is a system 100 for monitoring gas emissions within a geographic area, such as a landfill. For convenience, the geographic area will be referred to as a landfill although it should be realized that the geographic area may be any area for which environmental monitoring is desired (e.g., gas or water pipeline, soil or groundwater monitoring, and the like). In one embodiment, the landfill (i.e., geographic area) is monitored for methane emissions, although system 100 may be used to monitor other gases or environmental conditions. System 100 includes a location detecting device 104. Location detecting device 104 is configured to determine a geographic location of the device 104 within the landfill as location detecting device 104 is moved or transported within the landfill.

Location detecting device 104 may include a global positioning system that determines a geographic location within the landfill based on signals received from a plurality of satellites and/or based on signals received from one or more towers as described herein. In some embodiments, location detecting device 104 includes an accelerometer or speedometer to determine how quickly the device is moved within the landfill and/or along a defined trajectory within the landfill. The geographic location determined by location detecting device 104 may include the global coordinates (i.e., longitude and latitude) of the device. In some embodiments, the geographic location may include relative coordinates (e.g., with respect to a corner or center of a landfill or a specific location or region), may include a distance from a specific location or region (e.g., a location or region with previous emission measurements exceeding a threshold), and the like. Location detecting device 104 may continuously or regularly detect the geographic location of the device as the device is moved. For example, in some instances, geographic location information is detected each time emission data is gathered or at sequential periods of time, such as every ½ second, every second, every 10 seconds, and the like.

Location detecting device 104 also includes a display 120 for displaying various information to a surveyor and/or receiving various inputs from the surveyor. For example, display 120 may be a touchscreen device that receives inputs from the surveyor via one or more selectable buttons 128. Location detecting device 104 may include an additional inputs, such as a keypad 122, that allow the user to input various pieces of information, such as date and time information, site-specific information (e.g., a landfill name, an owner's name, or a landfill's address), summary variables, location information (e.g., relating to locations of specific emission measurements), emission measurements and/or variables relating to emission measurements (e.g., binary outputs indicating whether emission measurements exceed a threshold or average emission measurements), and the like. As described herein, in other embodiments, some or all of this information may be provided to system 100 from an external system, such as by downloading this information from a network, and the like. Location detecting device 104 may also include a trigger button 124 that may be operated to activate a gas emissions measurement, geographic location measurements, transmittal of gas emissions data, and the like. Trigger button 124 may be a soft key displayed on display 120 and/or may include a hard key of keypad 122. Additional aspects of location detecting device 104 are provided in the description of FIG. 4.

System 100 also includes an emission-detecting device 102. Emission-detecting device 102 is configured to sample surrounding air as the emission-detecting device is moved or transported within the landfill. Emission-detecting device 102 may be a device separate from location detecting device 104 as shown in FIG. 1, or may be a component of a single unit or device. The separate emission-detecting device 102 and location detecting device 104 may communicate wirelessly (e.g., via Bluetooth, and the like), or by one or more wired connections.

Emission-detecting device 102 is used to detect a quantity and/or concentration of one or more gases within the sampled air. Emission-detecting device 102 may include an analysis component that assess the components of the sample air to detect/determine a quantity, concentration, and the like of one or more gases, such as methane. Emission-detecting device 102 may include a gas-chromatography subcomponent, a mass-spectroscopy subcomponent, an absorption spectrometer, a photoionization detector, a (e.g., thermal, electrolytic conductivity detector, and/or flame-ionization detector), and the like. Emission-detecting device 102 may include a hydrogen tank 130 as shown and described herein, a handle 132 for transport, a display and/or input component 134, and the like.

To receive surrounding air that is to be sampled, emission-detecting device 102 may include or be fluidly coupled with an air sampling device 106. Air sampling device 106 includes a rod having a handle 146 that may be grasped by the surveyor. Rod 142 is coupled with or otherwise includes a gas sampling tube 140 that is fluidly coupled with emission-detecting device 102. Gas sampling tube 140 includes a gas inlet port 148 through which air is received and routed to emission-detecting device 102 for sampling. In one embodiment, rod 142 includes a trigger 144 that may be activated to initiate a gas sampling procedure, such as those described herein.

Gas sampling tube 140 may be coupled with rod 142 so that gas inlet port 148 is positioned a distance X from the distal end of rod 142. In this manner, when the distal end of rod 142 contacts the ground of the landfill, gas inlet port 148 is positioned a desired distance above the ground for gas emissions sampling. Thus, a user may conveniently grasp rod 142, contact the ground with the distal end of rod 142, and operate a trigger (e.g., 144 or 124) to initiate an air sampling procedure. Distance X may correspond to a specified distance for gas emissions sampling. In some embodiments, distance X may be between about 1 and 10 inches, and more commonly between about 2 and 4 inches or approximately about 3 inches. In other embodiments, rod 142 may include a port or aperture and a lumen that fluidly couples with or encases gas sampling tube 140.

In other embodiments, emission-detecting device 102 does not receive surrounding air via air sampling device 106. Instead, an air-monitoring assessment may be conducted remotely outside of the emission-detecting device 102. For example, emission-detecting device 102 may emit a heat or optical source that would interact with methane gas if it were present, e.g., in a concentration-dependent manner. An analysis component (e.g., a light or heat detector) may assess any such interaction.

System 100 may also include a processor (not shown) that may receive results from the emission-detecting device 102 and/or location detecting device 104. The processor may calculate a predicted gas quantity and/or concentration based on the received results. The processor may also determine error bars or confidence intervals and/or relate the calculated concentration to a threshold (e.g., by noting calculated concentrations exceeding the threshold). One or more summary variables may be determined by the processor. Examples of summary variables may include an overall compliance or non-compliance variable, a number of over-threshold emission locations, and/or an average emission measurement. The processor may also associate the gas sampling results (e.g., a quantity and/or concentration of methane) with a corresponding geographic location of the landfill determined or measured by location detecting device 104. The processor may perform this gas sampling results/geographic location association process any number of times to provide gas emissions data for the landfill. The processor may be a component of a computing device that performs this association and/or other processes.

In some embodiments, the computing device and processor may be components of the location detecting device 104 or emissions-detecting device 102. The gas sampling results may be transmitted (e.g., via wired or wireless communication) to location detecting device 104, or alternatively the geographic location information may be transmitted to emissions-detecting device 102, so that the computing device can associate the emissions results with the geographic location of the sampling. In another embodiments, the computing device is a component of a device and/or system located remotely from the landfill. The remotely located device or system may receive the gas sampling results and/or geographic location information from devices 102 and/or 104 and associate the gas samples with the corresponding geographic locations to provide gas emissions data for the landfill. This information (i.e., the gas sampling results and/or geographic location information) may be received in real time as the sampling is taking place or at any other time, such as when one or more sampling processes is complete.

System 100 may also include a communication device or component (not shown) that communicates with one or more other external devices, such as the remotely located computing device and processor. The communication device or component may communicate information about the determined geographic locations and air samples results within the landfill. In one embodiment, the computing device, location detecting device, and communication device are all components of location detecting device 104. This single device wirelessly receives gas sampling results information from emissions-detecting device 102 and associates the results with the determined geographic location information to produce gas sampling data points that may be documented and monitored.

Figure 2:
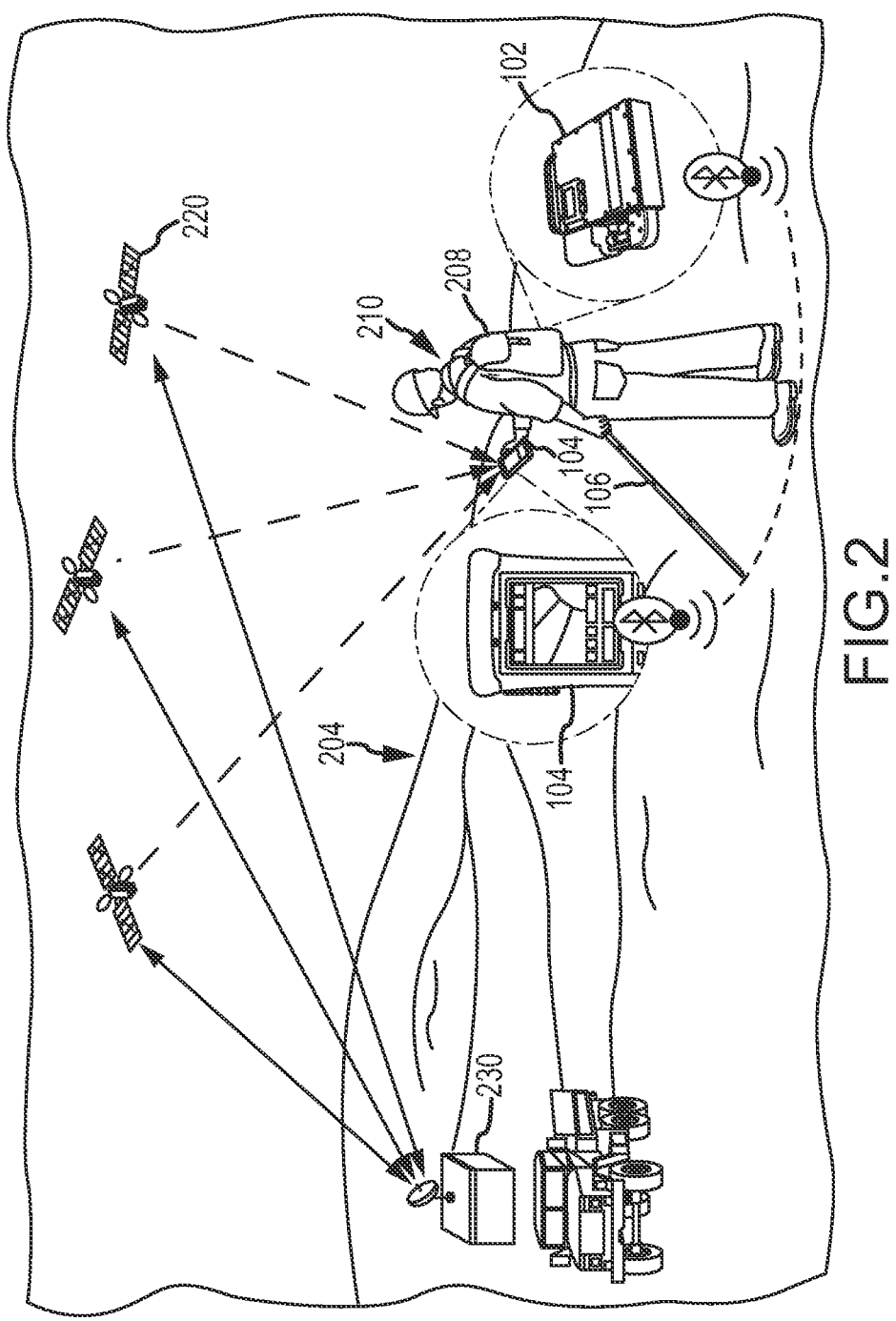
FIG. 2 illustrates a perspective view of the system of FIG. 1 being used to monitor gas emission in a landfill.

Referring now to FIG. 2, shown is the system 100 of FIG. 1 being used in a landfill 204 to monitor gas emissions from the landfill 204. Specifically, a surveyor 210 is holding location detecting device 104 in one hand while grasping a proximal end (e.g., handle 146) of air sampling device 106. The distal end of air sampling device 106 is positioned slightly above the ground of the landfill 204. Surrounding air is drawn into an air inlet port of air sampling device 106 and routed to emissions-detecting device 102 (e.g., via gas sampling tube 140). Emissions-detecting device 102 is being supported or carried within a backpack 208 worn by surveyor 210. In this manner, system 100 is portable and surveyor 210 is able to easily transport the various devices and/or components of system 100 along a defined route in landfill 204.

Location detecting device 104 wirelessly transmits and/or receives (e.g., via Bluetooth) various communications, instructions, information, and the like with emissions-detecting device 102 as described herein. For example, emissions-detecting device 102 may transmit the air sampling results to location detecting device 104 so that a computing device (not shown) of location detecting device 104 may associates determined geographic location information with the air sampling results as described herein.

To determine the geographic location information, and/or transmit and/or receive various information from one or more external systems or devices, location detecting device 104 may wirelessly communicate (e.g., via a communication device) with one or more satellites 220 and externally located systems or land based devices 230. For example, external system or land based device 230 may provide location correction information to device 104 to allow for more accurate determination of the location of device 104. This location correction information can be sent from device 230 or from satellites 220 by various wirelessly communication methods. Devices 230 may also be configured to transmit and or receive various information from device 104. In addition, gas sampling data may be transmitted (e.g., either in real time, at specified time periods, or all at one time) from location detecting device 104 to an external system or device 230. External system or device 230 may include a system or device of an owner of the monitored site. Similarly, various information may be transmitted to location detecting device 104, such as landfill or other geographic boundaries, site specific information, specific locations within the landfill that need to be re-monitored or re-sampled (e.g., specific locations having previous high gas emission readings), a trajectory along which the system 100 is to be moved or transported within landfill 204 to sample gas emissions, and the like.

In one embodiment, device 230 comprises a satellite correction system that includes information used by location detecting device 104 for real time kinematic correction to provide accurate locations detection. In this embodiment, device 230 may only transmit information to location detecting device 104. In another embodiment, device 230 may be a computer or server of the owner of the monitored site or a company providing service to system 100. In this embodiment, device 230 may transmit and/or receive information from location detecting device 104.

Although the external systems or devices 230 shown in FIG. 2 have been describe as wirelessly communicating with location detecting device 104, it should be realized that in some embodiments emissions-detecting device 102 may communicate with the external systems or devices 230 or such systems may communicate with a single device that includes both location detecting device 104 and emissions-detecting device 102.

Figure 3:
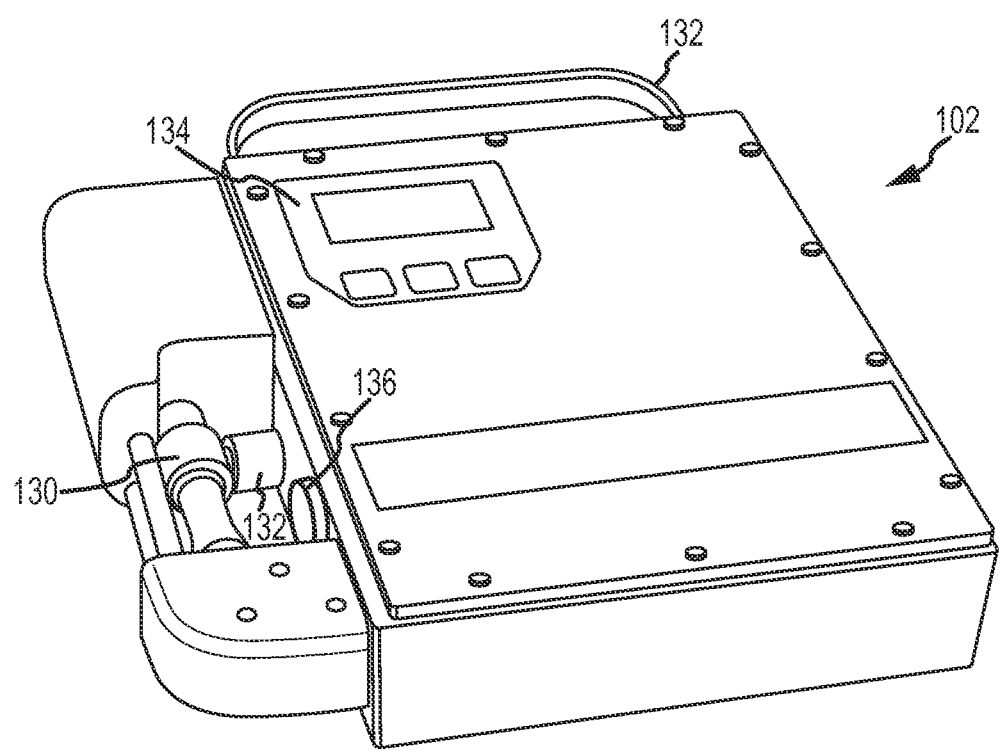
FIG. 3 illustrates an emissions-detecting device or component of the system of FIG. 1 according to an embodiment of the invention.
Figure 7:
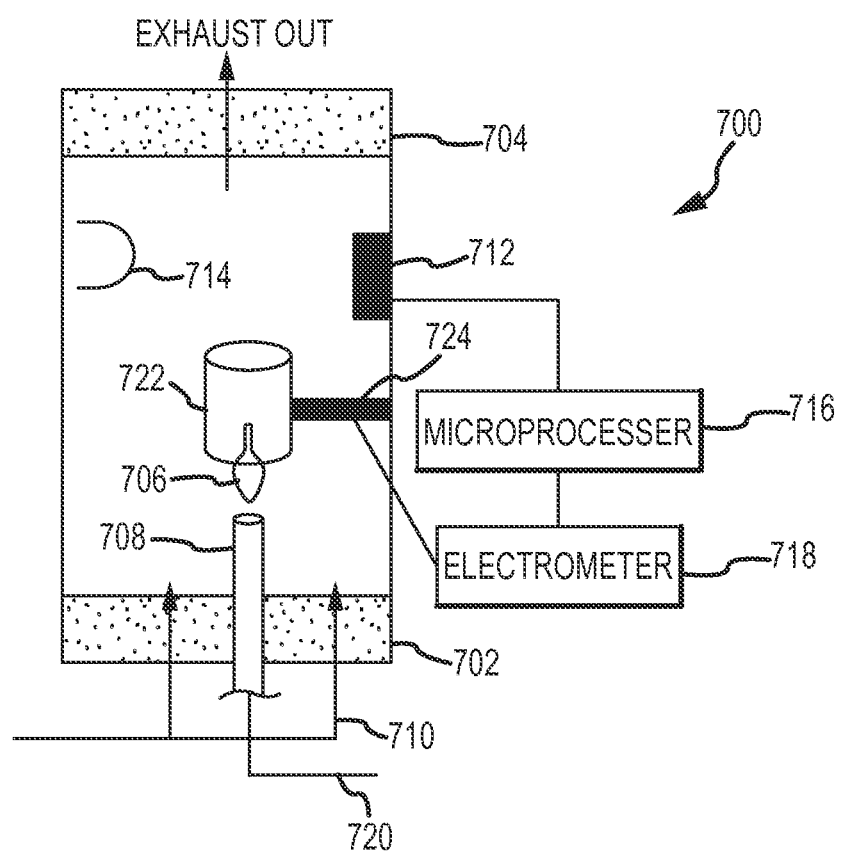
FIG. 7 illustrate a flame ionization device or component of the emissions-detecting device or component of FIG. 3 according to an embodiment of the invention.

Referring now to FIGS. 3 and 7, illustrated is a perspective view of emissions-detecting device 102 including handle 132, display and/or input component 134, and hydrogen tank 130. In the embodiment shown in FIG. 3, emissions-detecting device 102 may use flame ionization detection (FID) to measure hydrocarbons (e.g., methane) and other combustible organic compounds in the air at parts per million (PPM) levels. Hydrogen tank 130 may include an on/off valve 132 that is used to provide the fuel for the flame 706 of an FID chamber 700. An embodiment of FID chamber 700 is shown in FIG. 7.

Emissions-detecting device 102 includes a built-in pump (not shown) that may continuously draw air into FID chamber 700, such as by drawing air through the gas inlet port and gas sampling tube of air sampling device 106. As shown in FIG. 7, combustible material (e.g., volatile organic compounds (VOC)) 710 are drawn into FID chamber 700. FID chamber 700 includes a proximal flame arrestor 702 adjacent an inlet port and a distal flame arrestor 704 adjacent an exhaust port that prevent flames from escaping FID chamber 700. Hydrogen gas 720 is supplied to flame 706 via hydrogen supply tube 708. The combustible material 710 (e.g., methane) in the sample air burns in the flame 706 of FID chamber 700. FID chamber 700 includes a detector 722 that provides an electrical signal proportional to the combustible material 710 in the sample air. For example, detector 722 may collect ions from the combusted VOCs. The ions may be exposed to an electric field thereby generating a current proportional to the number of ions in detector 722.

The generated electrical signal may be transferred (e.g., via connection 724) to an electrometer 718 to convert the signal to an equivalent PPM measurement for the combustible material 710. The conversion of the signal to an equivalent PPM measurement may be based on a corresponding reading of a calibration gas. Electrometer 718 may be communicatively coupled with a microprocessor 716, such as the processor and/or computing device described above, to provide the PPM measurements and/or signal to microprocessor 716 for analysis and/or display to a surveyor. The sample air and combusted VOCs 710 may be exhausted from FID chamber 700 through distal flame arrestor 704 and out an exhaust port (not shown) of emissions-detecting device 102.

FID chamber 700 may also include a thermocouple 714 for measuring the temperature of FID chamber 700 and may also include a glow plug 712 that is used to ignite flame 706. Microprocessor 716 may be communicatively coupled with glow plug 712 to provide a flame ignition signal. Flame 706 may be ignited via a user input on input device 134 and/or by user input wirelessly transmitted from location detecting device 104. In this manner, the user can ignite flame 706 even when emissions-detecting device 102 is carried and/or transported within a backpack. In this manner, flame 706 of FID chamber 700 need only be ignited when gas sampling is to occur, thereby minimizing usage of hydrogen fuel from hydrogen tank 130 and/or prolonging operational usage time of emissions-detecting device 102. In addition, flame 706 may be restarted via wireless communication from location detecting device 104 in case the flame burns out or extinguishes during operation. In some embodiments, emissions-detecting device 102 may have a response time of less than 5 seconds, and more commonly less than 3 seconds and/or 1 second. Emissions-detecting device 102 may also have an operating concentration range of between about 0.1 ppm and about 50,000 ppm.

In some embodiments, hydrogen tank 130 comprises a metal hydride storage matrix for storing the hydrogen gas. In some embodiments, hydrogen tank 130 may provide between about 60 and about 80 hours of use per filling, and more commonly about 70 hours of use. Hydrogen tank 130 may also provide the hydrogen gas at a pressure of 100 pounds per square inch (psi) or less and, in some embodiments, 80 psi or less. This design may allow a user of emissions-detecting device 102 to operate the device for longer periods between refills and/or only refill hydrogen tank 130 with hydrogen gas once per week. The metal hydride storage matrix of hydrogen tank 130 may include a metal surface or interface region onto which hydrogen gas is adsorbed. The adsorbed hydrogen gas may dissociate into individual hydrogen atoms and diffuse or dissolve into the metal lattice of the metal hydride storage matrix. Within the metal lattice, the hydrogen atom may arrange into a specific configuration and form a metal hydride phase. Such a configuration may allow hydrogen tank 130 to have a shipping classification (e.g., UN 3468) that allows the tank to be shipped via air cargo full of hydrogen.

Emissions-detecting device 102 may also include a battery (not shown) to provide operational power to the device. In some embodiments, the battery may include a nickel-metal hydride cell (NiMH) battery that provide between about 14 and 18 hours of use, and more commonly about 15 hours. Such batteries may allow a user to perform multiple shifts without requiring a new battery. The NiMH battery of emissions-detecting device 102 my be charged with a smart charger that monitors and/or records the status of the battery during recharge, informs a user if a connection with the battery is not established, and the like. The smart charger may allow the battery to fully charge in less than about 4 hours in some embodiments, and more commonly less than about 2 hours.

Emissions-detecting device 102 may also include an alarm 136 that may be triggered when emissions-detecting device 102 detects the presence and/or a defined quantity or concentration of one or more specified gases in the sampled air. The trigger level (e.g., defined quantity, concentration, and the like) for alarm 136 may be preset by the user via input device 134 and/or via a separate device, such as location detecting device 104. Alarm 136 may alert that surveyor that the gas emissions level in a particular area of the landfill exceed a defined amount so that the surveyor may switch the operational mode of emissions-detecting device 102 as described above and conduct a more thorough monitoring of the location.

Figure 4:
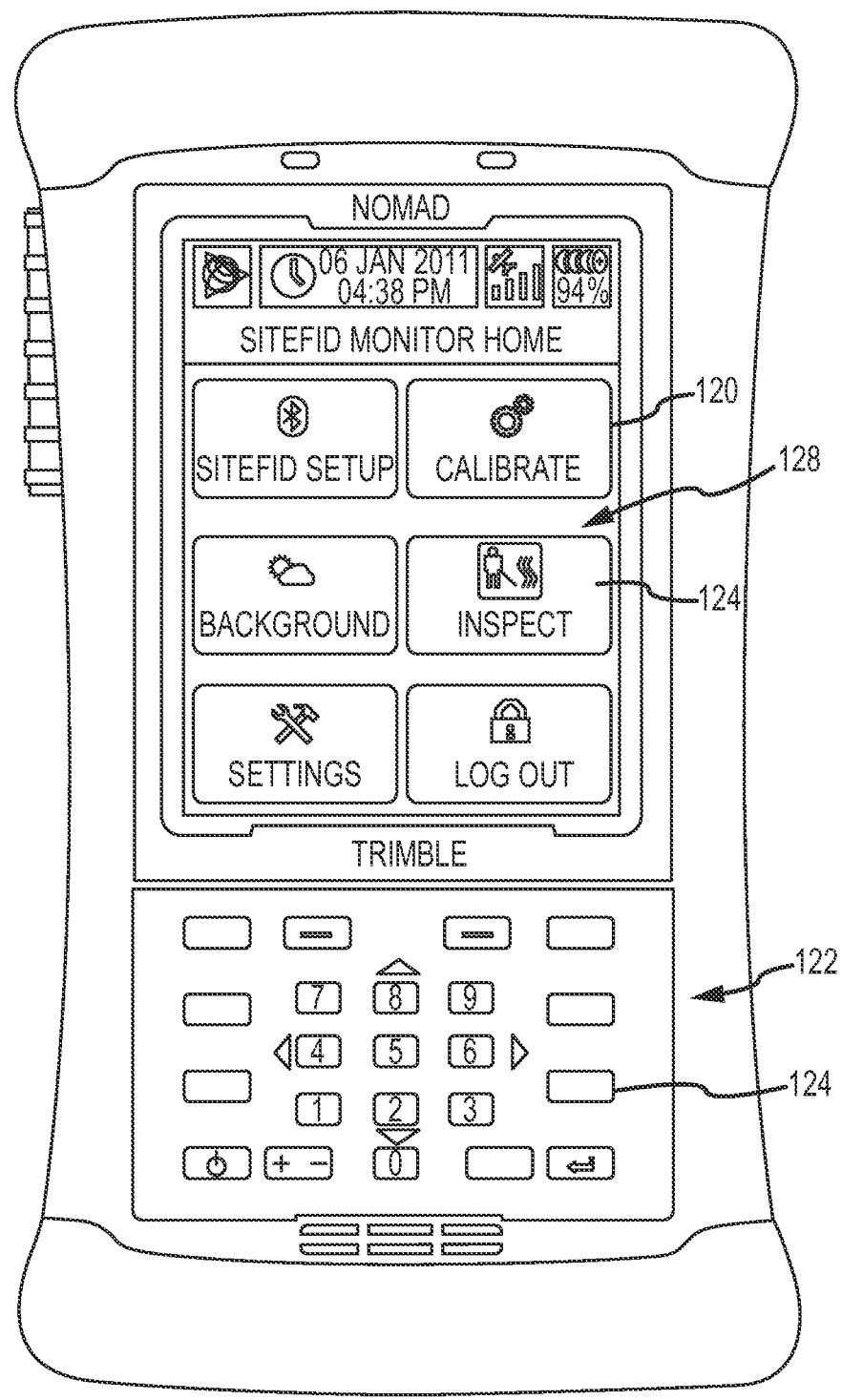
FIG. 4 illustrates a location detecting device or component of the system of FIG. 1 according to an embodiment of the invention.

Referring now to FIG. 4, illustrated is an embodiment of location detecting device 104. As previously described, location detecting device 104 may include keypad 122, display 120, trigger 124, and/or one or more selectable buttons 128 displayed on display 120. Location detecting device 104 may be wirelessly connected to emissions-detecting device 102 to allow location detecting device 104 to control emissions-detecting device 104. For example, as previously described, flame 706 of FID chamber 700 may be lit and or re-ignited via input commands entered by a user on location detecting device 104. Similarly, trigger levels for alarm 136, gas emissions detection levels, gas emissions sampling intervals, and the like may be input by the surveyor via location detecting device 104 and wirelessly communications to emissions-detecting device 104 to control the operation of the device. Alternatively, one or more of these operational controls may be received at location detecting device 104 via an external source, such as a central system.

Location detecting device 104 may also include a battery (not shown) that provides operational power to location detecting device 104. In some embodiments, the battery may be a lithium ion battery that provide 12 hours or more of operational use. In some embodiments, location detecting device 104 may be configured to be transported by hand (or by some other method) within a landfill or other geographic area. Location detecting device 104 may include a computing device (not shown) that calculates gas emission data by receiving monitored gas emission levels from emissions-detecting device 102 and associating the monitored gas emissions with geographical coordinates (i.e., longitude and latitude) of the monitored location. Location detecting device 104 may wirelessly transmit the gas emissions data to one or more external devices or sources, such as an external database, an owner of the monitored site, and the like. In some embodiments, location detecting device 104 includes a storage medium or device for storing the gas emissions data. This gas emissions data may then be uploaded to one or more compliance and/or reporting systems after the monitoring process is complete. Similarly, the data may be loaded into one or more analysis applications, such as a spreadsheet and/or CAD or GIS application for graphical display of the sampling results. Location detecting device 104 may automatically activate operation of a gas sampling process, such as when device 104 detects that a boundary has been crossed or reached, and/or may activate the gas sampling process when an input is received from a surveyor. In one embodiments, location detecting device 104 triggers the gas sampling process at sequential time intervals, such as every ½ second, every second, every 10 seconds, and the like, and/or triggers the gas sampling process at sequential distances, such as every 10 yards, every 50 yards, every 100 yards, and the like. The accelerometer and speedometer may be used to determine when device 104 has traversed the specified sequential distances.

Figure 5A:
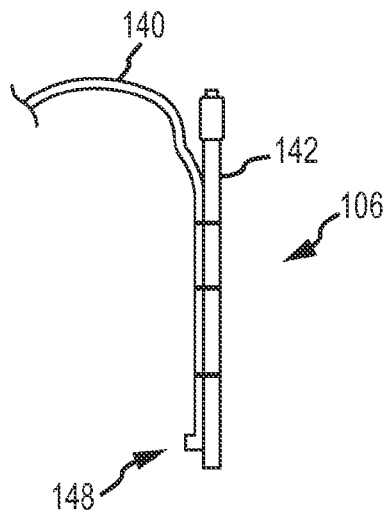
FIGS. 5A-C illustrate air sampling devices or components of the system of FIG. 1 according to embodiments of the invention.
Figure 5B:
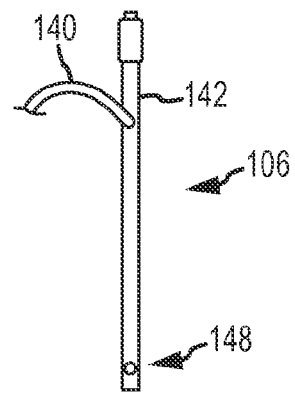
Figure 5C:
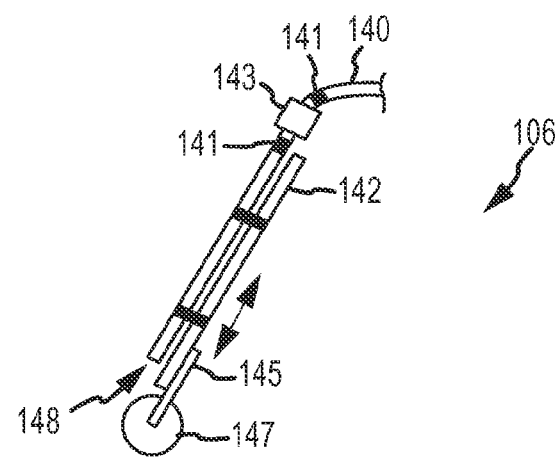

Referring now to FIG. 5A-C, illustrated are embodiments of air sampling device 106. FIG. 5A specifically shows air sampling device 106 having gas sampling tube 140 coupled with rod 142 so that gas sampling tube 140 extends along one side of rod 142. Disposed near a distal end of rod 142 is gas inlet port 148 that allows air to be drawn into gas sampling tube 140 and routed to emissions-detecting device 102. FIG. 5B shows an alternative embodiment of air sampling device 106 having air sampling tube 140 disposed within rod 142 or fluidly coupled with a lumen that extends between gas sampling tube 140 and gas inlet port 148 disposed at a distal end of rod 142. In some embodiments, gas inlet port 148 is positioned a defined distance from the distal end of rod 142 so that when the distal end of rod 142 contacts the ground, gas inlet port 142 draws in air at a defined distance above the ground.

FIG. 5C shows another embodiment of air sampling device 106 having air sampling tube 140 coupled with rod 142 so that gas sampling tube 140 extends along one side of rod 142. Disposed near a distal end of rod 142 is gas inlet port 148 that draws air into gas sampling tube 140. Disposed along the longitudinal length of gas sampling tube 140 may be one or more filters 143. Filter 143 may be a flat filter that can be easily visually inspected and replaced if needed. The canister housing filter 143 may be made of a clear material so that filter 143 can be visually inspected without opening the canister. Filter 143 may be coupled with gas sampling tube 140 via one or more quick connect fittings 141. In some embodiments, a second filter may be coupled with gas sampling tube 140 near an inlet port of emissions-detecting device 102. The second filter may be a Teflon filter. Rod 142 may also be coupled with an off-set rod 145 that is further coupled with a movement device, such as wheel 147. Off-set rod 145 may be adjusted longitudinally along or with respect to rod 142 so that the distance between the distal end of rod 142 and wheel 147 is increased or decreased. In this manner the distance of gas inlet port 148 above the ground surface may be adjusted to a desired height. Surrounding air may then be drawn into gas inlet port 148 at or around the desired height. Wheel 147 allows air sampling device 106 to be easily moved within the geographic area while maintaining gas inlet port 148 at the desired distance above ground.

Figure 6A:
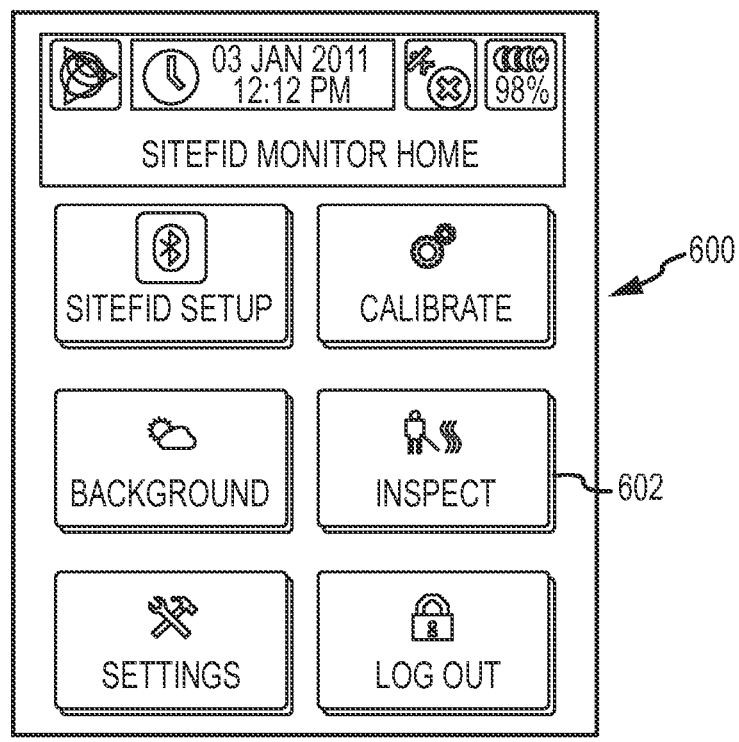
FIGS. 6A-G illustrate various screen view of the location detecting device or component of FIG. 4 according to embodiments of the invention.

Referring now to FIGS. 6A-G, illustrated are various screen views that may be displayed on display 120 representing various functionalities of location detecting device 104 and/or the gas monitoring system. FIG. 6A shows a main display 600 including various selectable buttons 602 that may be selected to perform one or more operations. Main display 600 includes a setup button that allows a user to set or define various parameters of location detecting device 104 and/or emissions-detecting device 102. Main display 600 also includes a calibration button that allows emissions-detecting device to be calibrated prior to performing gas emissions monitoring as described herein, a background button that records one or more background readings that may be recorded along with the gas emissions data, an inspect button that may be used to initiate the gas emissions monitoring process, a setting button that may allow various setting to be adjusted (e.g., alarm trigger settings, display settings, and the like), and a log out button that may log a user off the system or software.

Figure 6B:
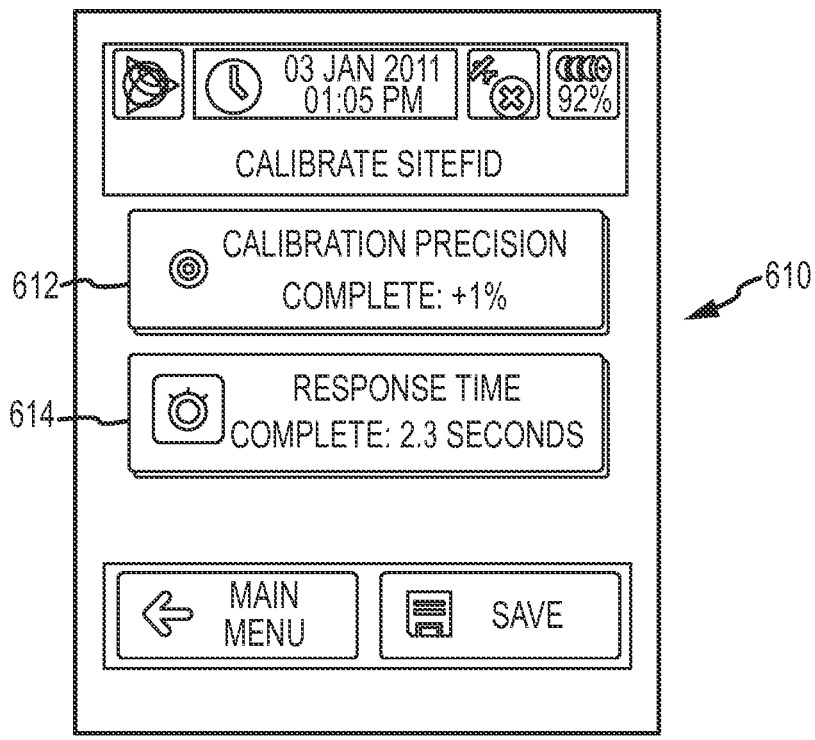
Figure 6C:
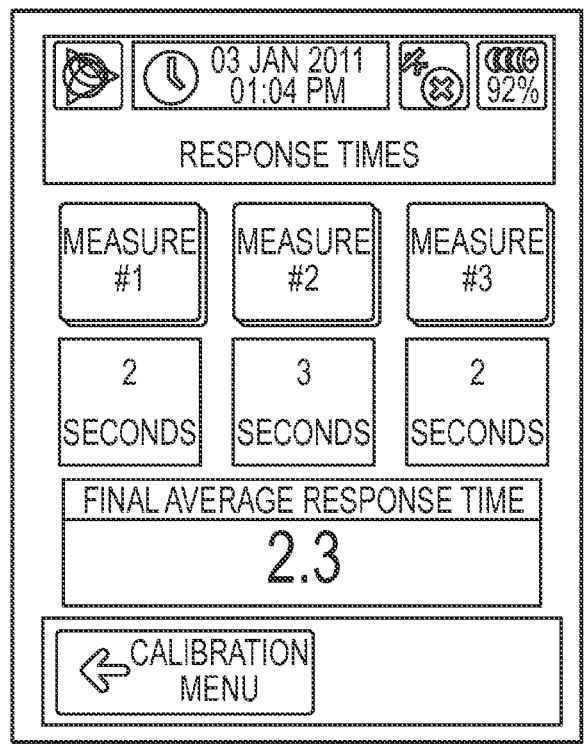

FIG. 6B shows a calibration display 610 that may be used during a calibration of the emissions-detecting device 102 as described herein. Calibration display 610 may include a calibration precision button 612 that shows the precision or accuracy of the calibration process and that may be selectable to conduct one or more calibration processes. Calibration display 610 may include a response time button 614 that shows the response time of gas emissions measurements. Selection of response time button 614 may result in display of a response time display 620 as shown in FIG. 6C. Response time display 620 may show the measured response time of one or more calibration measurements and/or may show a time average response time of the various measurements. In some embodiments, response time display 620 may be used to perform a gas emissions calibration process.

Figure 6D:
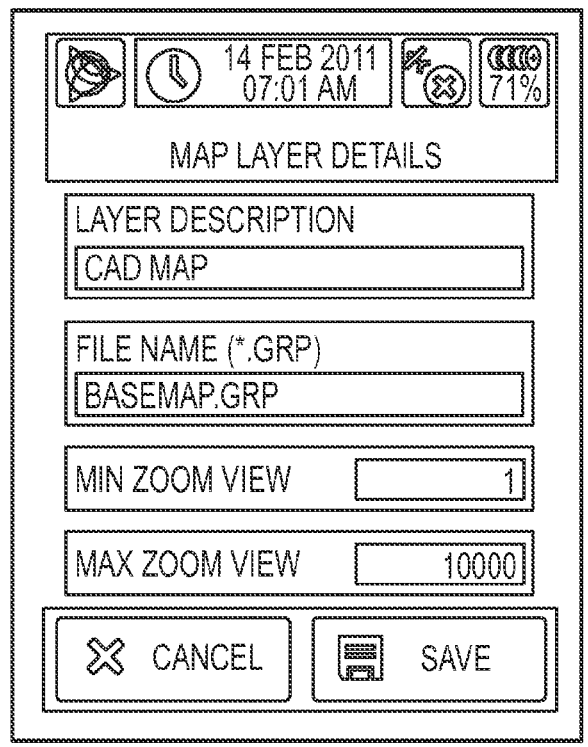
Figure 6E:
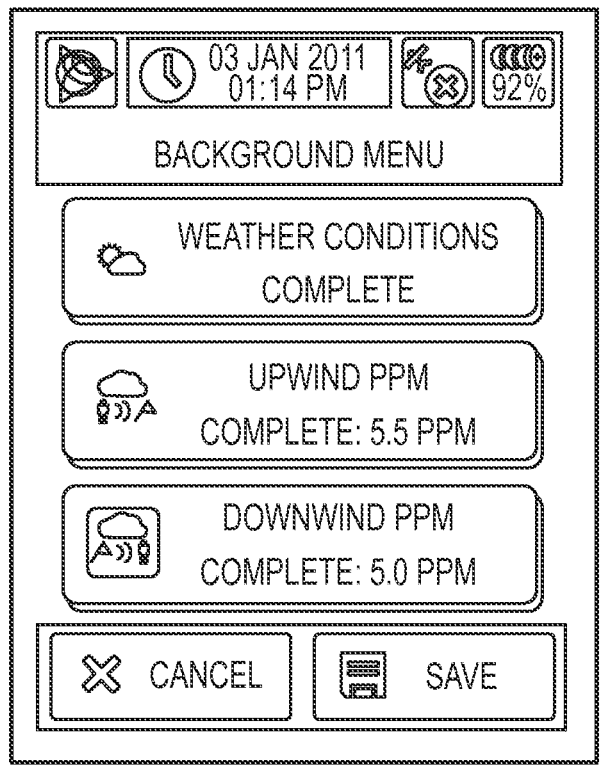

FIG. 6D shows a site-setup display 630 that may be used to download or upload one or more maps and/or used to enter various map parameters, such as map name, zoom levels, display settings, and the like. For example, a surveyor could input a filename of a map to upload a map of a geographic area, such as a landfill, from a storage medium of location detecting device 104. Alternatively, the user could download such a map from an external database or source via site-setup display 630. FIG. 6E shows background collection display 640. Background collection display 640 may display various environmental conditions of the geographic area being monitored, such as the upwind and downwind conditions and/or other weather conditions, such as relative or absolute humidity, temperature, and the like. Background collection display 640 may include various selectable buttons that automatically perform a background condition reading process or allow a surveyor to input a portion or all of this information. Background collection display 640 may also allow a surveyor to save or record the area's background conditions so that this information may be transmitted or used along with the gas emissions data.

Figure 6F:
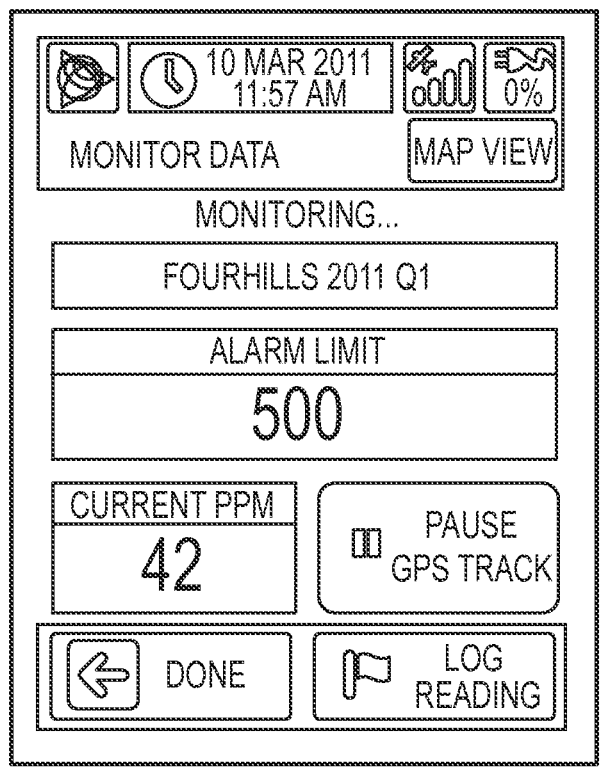

FIG. 6F shows a site monitoring display 650. Site monitoring display 650 may display real time monitoring conditions, such as a current gas emissions reading in parts per million and a current alarm trigger level (e.g., 500 PPM). Site monitoring display 650 may also allow a surveyor to start and stop a gas emissions monitoring process, change an operational mode of the monitoring device as described herein, log or record various data readings, upload and/or download gas emissions data, and the like.

Figure 6G:
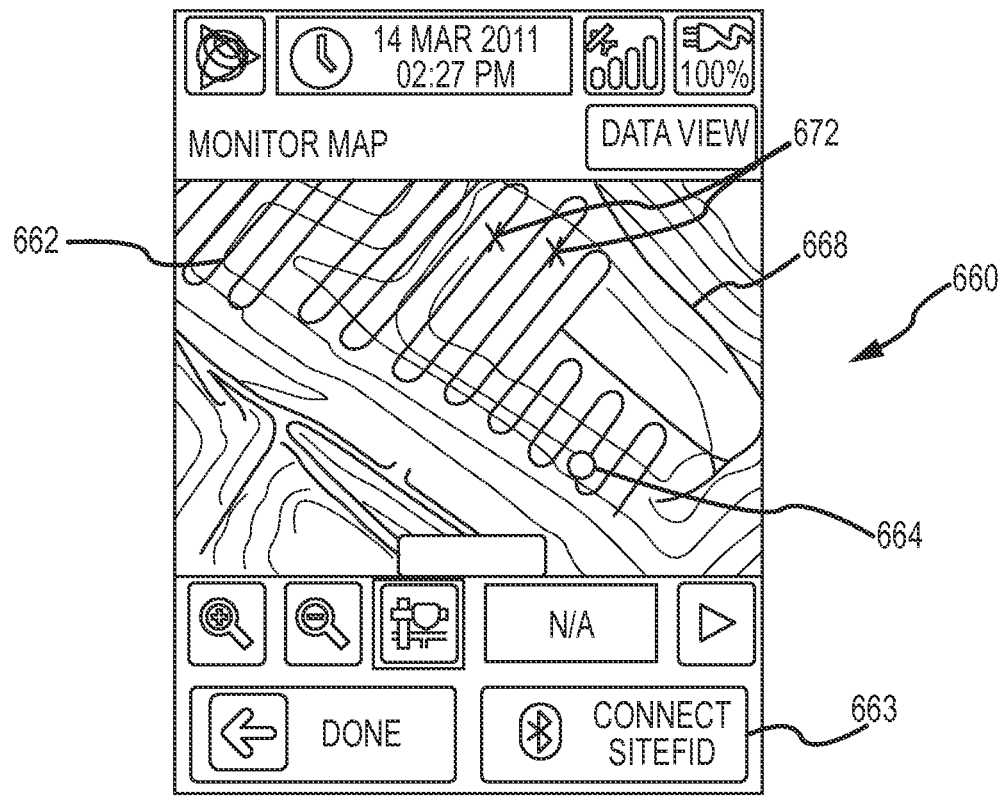

FIG. 6G shows a site navigation display 660 that may display a real time location 664 of the surveyor and may also show a defined trajectory or monitoring path 662 along which location detection device 104 and emissions-detecting device 102 are to be transport or moved. Site navigation display 660 may also display a boundary 668 of the landfill or other geographic area and various other features of the surrounding area, such as roadways, waterways, and the like. The defined trajectory or monitoring path 662 displayed on site navigation display 660 may be downloaded from an external source or device or uploaded from a storage medium of location detecting device 104. Site navigation display 660 may also display one or more markers 672 corresponding to areas with previously high or concerning gas emissions levels. Markers 672 may alert a surveyor to areas which may need additional monitoring or attention. In some embodiments, markers 672 may be displayed on site navigation display 660 in real time as one or more areas are detected having gas emissions that exceed a defined limit. Site navigation display 660 may also include one or more zoom buttons that allow a surveyor to zoom in and out of the display and focus on specific areas. Site navigation display 660 may also include a connection button 663 that is used to wirelessly connect location detection device 104 to emissions-detection device 102 to begin a gas emissions monitoring process.

Figure 8:
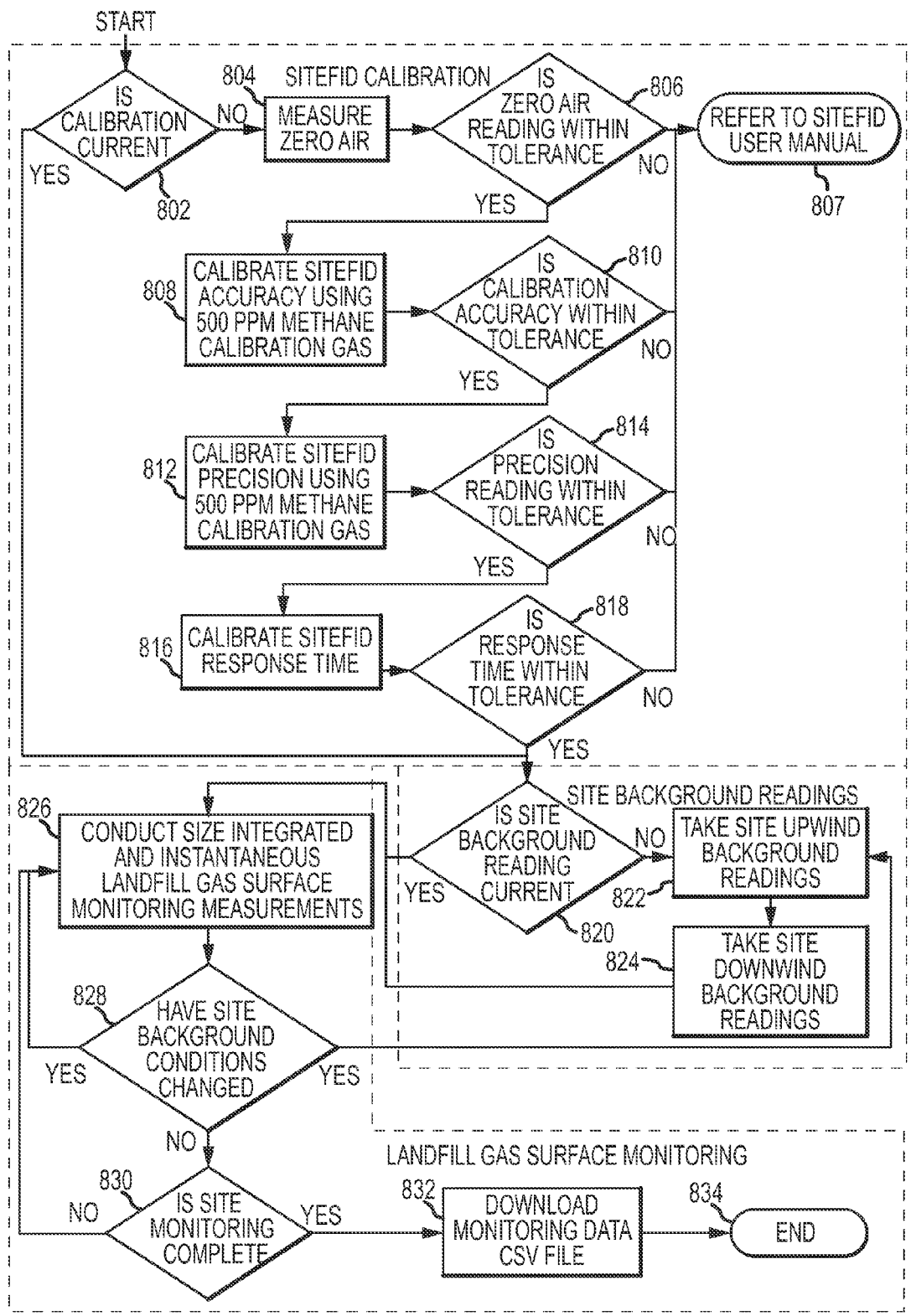
FIG. 8 illustrates a method of using a gas emissions monitoring system according to an embodiment of the invention.

Referring now to FIG. 8, illustrated is an embodiment of a method of using a portable gas emissions monitoring system to monitor gas emissions within a defined geographic area, such as a landfill. The gas emissions monitoring system may be similar to that described in FIG. 1 having a location detecting device, air sample device, and a emissions-detecting device. These devices may be separate devices or integrated as components into a single unit. In one embodiment, a surveyor may interact and provide input to a location detecting device that wirelessly communicates various instructions to a separate emissions-detecting device to perform the calibration, background readings, and/or monitoring processes described in FIG. 8, although, in some embodiments, these instructions may be directly input into the emissions-detecting device. The separate emissions-detecting device may likewise transmit gas emissions readings and data back to the location detecting device so that these readings and/or data may be associated with geographical coordinates (e.g., longitude and latitude) measured or determined by the location detecting device.

Referring now to method 800, at block 802, a determination is made about whether the emissions-detecting device or component is properly calibrated, such as if a calibration process was recently performed. If the emissions-detecting device is properly calibrated, the method may proceed to a background reading process beginning at block 820, otherwise, the method proceeds to block 804 to begin a calibration process. At block 804, the emissions-detecting device is used to measure zero air (i.e., atmospheric air containing less than 0.1 PPM total hydrocarbons). This measurement process may be initiated by the location detecting device or component. At block 806, it is determined whether the emissions-detecting device's zero air reading is within a defined tolerance, such as within 5% of accuracy, or within 1% of accuracy. If the zero air reading is within a defined tolerance, at block 808, the accuracy of the emissions-detecting device (i.e., the flame ionization detection device) is calibrated using a calibration gas, such as a gas containing 500 PPM methane. The accuracy of the emissions-detecting device may be calibrated to within a defined tolerance, such as within 5% of accuracy, 3% of accuracy, or within 1% of accuracy. For example, the calibration gas is a known value (e.g., 500 PPM methane) and the reading on device 102 is compared to the known reading. The accuracy of device 102 is then determined by the variance of the reading from the known value (e.g., a reading 505 PPM has an accuracy of 1% as it varies from the know value of 500 PPM by 5 PPM). At block 810, it is determined whether the accuracy of the emissions-detecting device is within a defined tolerance.

If the accuracy is within the defined tolerance, at block 812, the precision of the emissions-detecting device is calibrated using the calibration gas. At block 814, it is determined whether the precision of the emissions-detecting device is within a defined tolerance. The precision of device may be determined by taking 3 separate readings and averaging the variance form the known calibration gas value (e.g., averaging the variance from the 500 PPM calibration gas). Precision is a measure of the repeatability of measurements of device 102 around the known calibration value. The precision of the emissions-detecting device may be calibrated to within a defined tolerance, such as within 5%, 3%, and/or within 1% of precision. If the precision is within the defined tolerance, at block 816, the response time of the emissions-detecting device is measured. At block 818, it is determined whether the response time of the emissions-detecting device is within a defined tolerance. At block 807, if any of the measurements for zero air, accuracy, precision, and/or response time are not within the defined tolerance, the user may be directed to a manual or other procedure to correct any potential problems and/or ensure that the calibration process is being performed correctly. If the measured readings for zero air, precision, accuracy, and response time are within the defined tolerances, the emissions-detecting device or component is properly calibrated and the method may proceed to reading background conditions and/or monitoring gas emissions for a geographic area.

At block 820, it is determined whether the background readings of the geographic area are current. For example, background readings may be required to be taken once a day, once an hour, at repeated sequential time intervals (e.g., every 4 hours), immediately prior to monitoring gas emissions, anytime conditions change, and the like. If the background readings are current, the method may proceed to block 826 to monitor gas emissions. If the background readings are not current, the method may proceed to block 822 to read one or more background conditions. At block 822, the upwind background readings may be measured and/or recorded and at block 824 the downwind background readings may be measured and/or recorded. Additional background readings may likewise be measured and/or recorded, such as humidity, air pressure, temperature, and the like.

At block 826, the geographic area (e.g., landfill, gas pipe, and the like) may be monitored for gas emissions as described herein. For example, a user may traverse along a prescribed path and take sequential or continuous readings of the gas emissions. These readings may be associated, via an internal or external computing device, with geographic locations measured or determined by a location detecting device as described herein. The associated data (e.g., geographic locations and gas emissions measurements) may represent gas emissions data for the geographic area. Monitoring the geographic area may involve conducting detailed monitoring of one or more locations within the geographic area, such as when gas emissions are detected that exceed a predefined level and/or when one or more locations are to be monitored to determine if a gas emissions reduction procedure is working The monitoring mode of the emissions-detecting device can be switched to pause a general monitoring operation and perform the detailed monitoring operation.

At block 828, it is determined whether the background readings of the geographic area have changed such as, for example, if wind direction, humidity, temperature, and the like have changed. If the background readings have changed, the process may proceed back to block 822 to re-measure and/or record the current background conditions, and/or the process may proceed back to block 826 to re-monitor the geographic area. At block 830, it is determined whether monitoring the geographic area is complete. If monitoring is not complete, such as if only a single area of multiple areas has been monitored, the process proceeds back to block 826 to monitor other areas and/or re-monitor specific locations within the geographic area. If monitoring is complete, the process proceeds to block 832 where the monitored gas emissions data may be downloaded to one or more databases and/or systems. For example, the gas emissions data may be wirelessly transmitted to an owner of the facility and/or transmitted to a database for further analysis, processing, documentation, and the like. After the gas emissions data is downloaded, the process ends at block 834.

Figure 9:
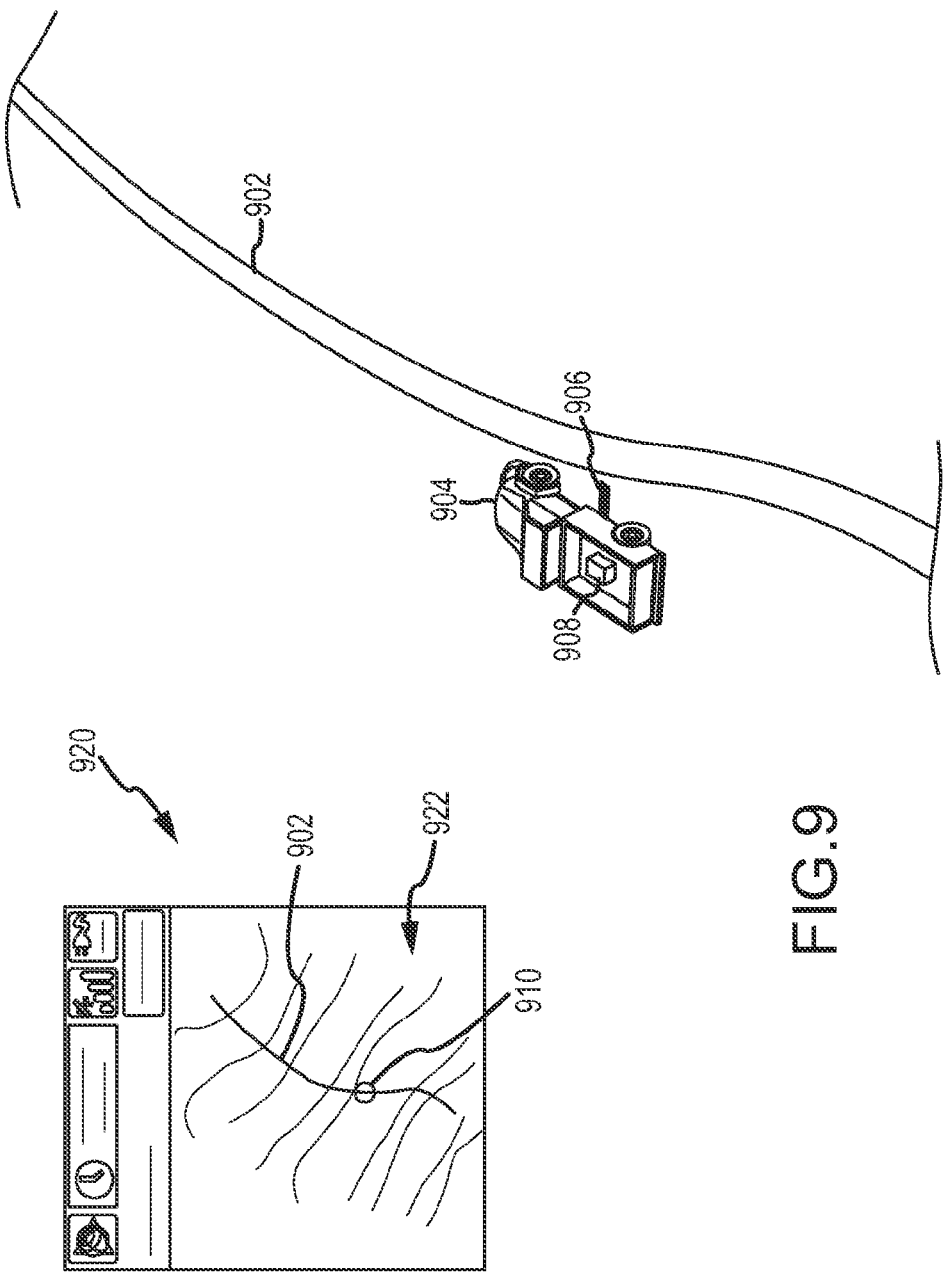
FIG. 9 illustrates a gas emissions monitoring system being used to monitor gas emissions from a buried gas pipeline according to an embodiment of the invention.

FIG. 9 illustrates another embodiment of a portable monitoring system being used to monitor gas emissions (e.g., methane) from a buried gas pipeline. Buried gas pipelines can develop a leak and allow gas to leak into the surrounding soil. The gas may then migrate through the soil to the surface and into the atmosphere. The monitoring systems described herein may analyze total volatile organic compounds (TVOCs) leaking from the gas pipeline and through the soil, including methane which is the main compound in natural gas. The detection of elevated levels of gas emission near the ground surface may alert a user of a potential leak from the pipeline.

FIG. 9 shows a vehicle 904 traversing along a path 902 of a geographic area that corresponds to a buried gas pipeline (not shown). Coupled toward the bottom of vehicle 904 is an air sampling device 906 that draws surrounding air into a gas sampling lumen (not shown) and/or provides the air to an emissions-detecting device (not shown) to analyze the air and measure a quantity and/or concentration of gases in the air. Air sampling device 906 may be coupled with vehicle 904 to be a set distance above the ground, such as about 1 to 20 inches above ground and in some embodiments about 2 to 5 inches above the ground, so that air is drawn into air sampling device 906 at or surrounding the set distance above ground. The emissions-detecting device may be a component of a device 908 that is carried or transported in vehicle 904. Device 908 may also include a location detecting device/component that measures and/or determines a geographic location of vehicle 904 as it moves along path 902. Device 908 may log or record the gas emissions readings as vehicle 904 moves along path 902 and associate the readings with the measured geographic locations. An operator of vehicle 904 may be alerted when gas emission readings exceed a defined level so that the operator can conduct more thorough monitoring of the area and/or document areas of high gas emissions. In some embodiments, gas emissions sampling results can be recorded at intervals of approximately one second, ½ seconds, every 3 seconds, and the like, although various other intervals may be used.

The gas monitoring system (e.g., device 908) may allow the upload of the gas pipeline and corresponding geographic area. Path 902 and the corresponding geographic area 922 can be displayed to the operator of vehicle 904 on a display 920 that may be mounted within the vehicle's cab. The current location 910 of vehicle 904 may be displayed in relation to geographic area 922 and path 902 so that the operator is aware of the route to traverse along the buried pipeline. The gas monitoring system (e.g., device 908) may also inform the operator of vehicle 904 of a speed at which to move along path 902, such as between about 5 and 10 miles per hour.

As shown in FIG. 9, gas pipeline monitoring can be conducted from vehicle 904, by the field worker walking along path 902, and the like. If an elevated gas emissions reading is detected during the pipeline monitoring the field worker can stop and use the gas monitoring system to verify the initial reading. The gas monitoring system can then be used to define the magnitude and extent of the elevated gas emissions readings. The site investigation of an elevated gas emissions reading can be done rapidly with the gas monitoring system and all the sample locations and monitoring results recorded on the computing device of the gas monitoring system. The sampling results can then be documented and/or provided to an owner of the pipeline. The owner in turn may provide the documented or monitored results to an agency to prove that the pipeline was monitored and is in compliance with one or more regulatory standards. The monitored pipeline may be any type of pipeline including an upstream pipeline (e.g., extending between the wellhead and processing facility), a downstream pipeline (e.g., a pipeline that runs to a city or area), a distribution pipeline to residential and/or commercial structures, and the like.

The gas monitoring system provides for a rapid monitoring of gas pipelines for elevated levels of gas emissions, such as methane. A record of the pipeline monitoring sample results and locations is created. An area of interest can also be rapidly investigated and defined using the gas monitoring system. As described above, the system may be calibrated and background readings measured and recorded. In one embodiment, the calibration and/or alarm trigger may be set at between about 15 and 40 PPM, and more commonly between about 20 and 25 PPM, so that minute gas emissions are detected. This may allow the field worker to determine if any leak, even small leaks, are present in the pipeline.

Figure 10:
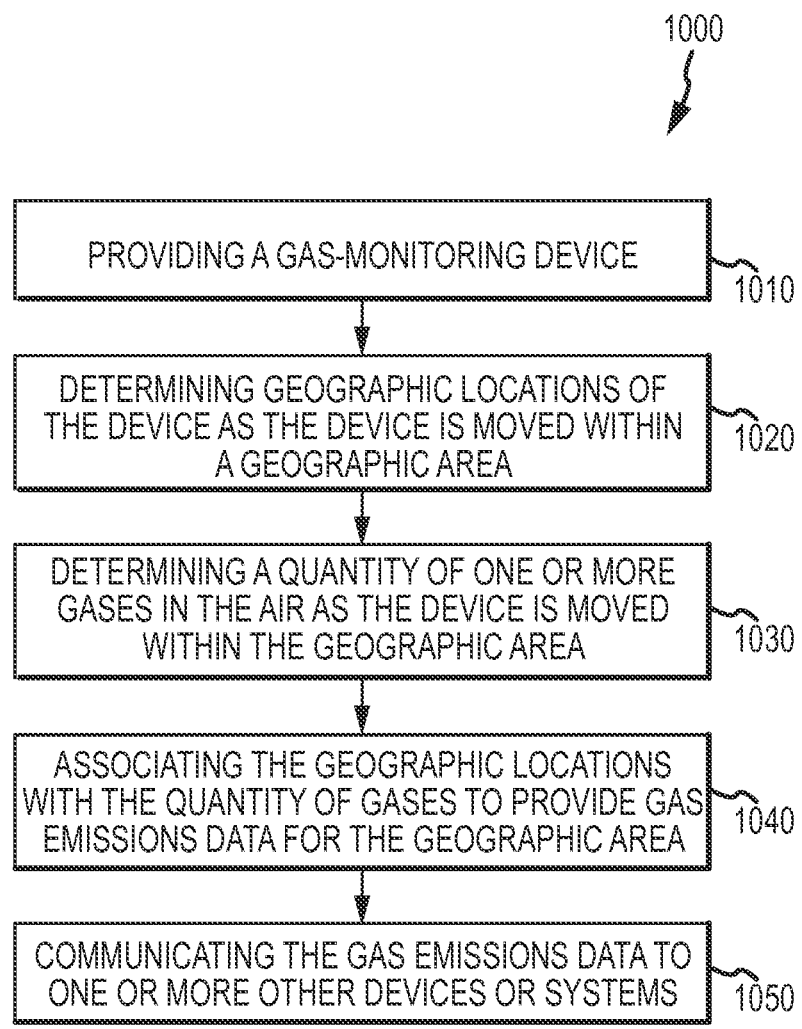
FIG. 10 illustrates a method for monitoring gas emissions from a geographic area according to an embodiment of the invention.

Referring now to FIG. 10, illustrated is an embodiment of a method 1000 for monitoring gas emissions within a geographic area (e.g., landfill, gas pipeline, and the like). At block 1010, a gas-monitoring device is provided. The gas-monitoring device is configured to be transported or moved within the geographic area to monitor gas emissions. At block 820, geographic locations within the geographic area are determined or measured with a location detecting component of the gas-monitoring device. The geographic locations are determined or measured as the gas-monitoring device is moved within the geographic area. At block 830, a quantity and/or concentration of one or more gases in the air is determined or measured with an emission-detecting component of the gas-monitoring device. Gas quantities and/or concentrations are determined or measured for each geographic location as the gas-monitoring device is moved within the geographic area. At block 840, a computing component of the gas-monitoring device associates the geographic locations with the quantity of one or more gases to provide gas emissions data for each geographic location where measurements are taken. At block 850, the gas emissions data is communicated via a communication component of the gas-monitoring device to one or more devices or systems. In some embodiments, communicating the gas emissions data to one or more external devices may include transmitting the gas emissions data to an owner of the facility or asset being monitored for gas emissions.

Method 1000 may further include displaying a map of the geographic area on a display device of the gas-monitoring device, plotting a path within the geographic area along which the gas-monitoring device is to be transported or moved, and/or displaying a data point for each geographic location where measurements are taken. In some embodiments, the path along which the gas-monitoring device is to be transported moved may be received from an external device, such as being wirelessly transmitted from a central computing system. The path along which the gas-monitoring device is moved may correspond to a buried gas pipeline or may be a path within a landfill. Method 1000 may further include alerting a user when the quantity of the one or more gases in the air exceeds a defined amount.

Method 1000 may additionally include re-sampling an identified geographic location within the geographic area when the quantity of the one or more gases of the identified geographic location exceeds a defined amount, the geographic location being identified by the computing component of the gas-monitoring device. Method 1000 may additionally include moving the gas-monitoring device along a path within the geographic area where the path corresponds to a buried gas pipeline and/or the geographic area corresponds to a landfill.

In some embodiments, the gas-monitoring device may activate the process of determining a quantity of one or more gases by determining: that the gas-monitoring device is located at a defined gas monitoring position, that a defined amount of time has passed since a previous air sampling, and/or that the gas-monitoring device has crossed a defined boundary of a trajectory along which the gas-monitoring device is moved. For example, the gas-monitoring device may be programmed with one or more locations for measuring gas-emissions and the device may recognize when the device is located at one of those locations, which automatically activates gas emissions measurements. Likewise, the gas-monitoring device may be programmed to measure gas emissions at sequential time periods (e.g., every 1 second, 5 second, 10 seconds, 1 minute, and the like), or may be programmed to automatically take emissions measurements when the device crosses programmed boundaries or landmarks.

As mentioned herein, the gas-monitoring device may be calibrated. In one embodiment calibrating the emission-detecting component of the gas-monitoring device may include determining that a reading of the emission-detecting component is within a defined tolerance when subjected to zero air and determining that one or more of the following is within a defined tolerance when subjected to a calibration gas: an accuracy of the emission-detecting component, a precision of the emission-detecting component, and/or a response time of the emission-detecting component. Background readings may also be taken with the gas-monitoring device and method 1000 may additionally include: determining one or more background air sampling conditions of the geographic area, the background air sampling conditions comprising either or both an upwind condition or a downwind condition; storing the one or more background air sampling conditions of the geographic area on a storage medium of the gas monitoring device; and communicating the one or more background air sampling conditions with the gas emissions data to the external device.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A gas-monitoring device transportable by a user within a geographic area to monitor gas emissions within the geographic area, the gas-monitoring device comprising:
    a handheld computing component having:
        a display for displaying information to the user;
        one or more inputs for receiving input from the user; and
        a location detecting component configured to determine a geographic location of the gas-monitoring device as the gas-monitoring device is moved within the geographic area; and
    an emission-detecting component separate from the handheld computing component and wirelessly coupled therewith so as to communicate information to the handheld computing component, the emission-detecting component being configured to sample surrounding air in a first mode of operation as the gas-monitoring device is moved along a predetermined path within the geographic area so as to monitor the gas emissions within the geographic area, wherein the predetermined path is a path for walking;
    wherein the handheld computing component further comprises a mode changing component that, upon actuation, initiates sampling of the surrounding air via the emission-detecting component in a second mode of operation for diverting from the predetermined path and determining of the geographic location via the location detecting component;
    wherein the handheld computing component is configured to plot the predetermined path on the display for a user to follow during emission detection; and
    wherein the handheld computing component is configured to associate monitored gas emissions information wirelessly received from the emission-detecting component with corresponding geographic location information provided by the location detecting component so as to provide gas emissions data for the geographic area.

2. The gas-monitoring device of claim 1, wherein the emission-detecting component further includes an air sampling instrument having a gas inlet port fluidly coupled with the emission-detecting component so as to provide air to the emission-detecting component for sampling.

3. The gas-monitoring device of claim 2, wherein the air sampling instrument comprises a rod and a gas sampling tube including the gas inlet port, the rod being configured to be grasped at a proximal end by a user, the tube having a proximal end fluidly coupled with the emission-detecting component and a distal end coupled with the rod so that the gas inlet port is positioned near a distal end of the rod.

4. The gas-monitoring device of claim 3, wherein the gas sampling tube is coupled with the rod such that when a distal end of the rod contacts the ground, the gas inlet port is positioned between 2 and 4 inches above the ground.

5. The gas-monitoring device of claim 1, wherein the handheld computing device further includes a communication component configured to communicate with an external device to transmit the gas emissions data to the external device.

6. The gas-monitoring device of claim 1, wherein actuation of a trigger causes the emission-detecting component to perform air sampling at regular intervals.

7. The gas-monitoring device of claim 1, wherein the emission-detecting component comprises a flame ionization detection device.

8. The gas-monitoring device of claim 7, wherein the emission-detecting component further comprises a metal hydride storage matrix for storing hydrogen gas for the flame ionization detection device.

9. The gas-monitoring device of claim 1, wherein the handheld computing component further comprises a storage medium for storing the gas emissions data for the geographic area.

10. The gas-monitoring device of claim 1, wherein the handheld computing component further comprises an analysis component configured to assess a quantity of one or more gases within the sampled air.

11. The gas-monitoring device of claim 1, wherein the geographic area comprises a landfill.

12. The gas-monitoring device of claim 1, wherein the gas-monitoring device is moved along the path within the geographic area, the path corresponding to a buried gas pipeline.

13. The gas-monitoring device of claim 1, wherein the handheld computing component is configured to provide instructions to the user of a speed the user is to travel on the predetermined path for measuring one or more gases in the air.

14. A system for monitoring gas emissions within a geographic area comprising:
   a handheld device having:
      a location detecting component configured to determine a geographic location of the handheld device as the handheld device is transported within the geographic area;
      a display for displaying a map of the geographic area to a user; and
      a communication component configured to communicate, with an external device, information about the determined geographic locations and air samples measured within the geographical area; and
   an emission-detecting device separate from the handheld device and wirelessly coupled therewith so as to communicate information to the handheld device, the emission-detecting device being configured to sample surrounding air in a first mode of operation as the emission-detecting device and handheld device are transported within the geographic area along a predetermined path so as to detect a quantity of one or more gases;
   wherein the handheld device further comprises a mode changing component that, upon actuation, initiates sampling of the surrounding air via the emission-detecting device in a second mode of operation for diverting from the predetermined path and determining of the geographic location via the location detecting component;
   wherein the handheld device is configured to plot the predetermined path for the user to follow;
   wherein the handheld device is configured to provide instructions to the user of a speed the user is to travel on the predetermined path for measuring one or more gases in the air; and
   wherein each of the air samples are associated with a corresponding geographic location within the geographic area so as to provide gas emissions data for the geographic area.

15. The system of claim 14, further comprising a computing device configured to associate the air samples with corresponding geographic locations to provide the gas emissions data.

16. The system of claim 15, wherein the computing device is located remotely from the geographic area, and wherein the computing device communicates with the communication device to receive the information about the determined geographic locations and the air samples within the geographical area.

17. The system of claim 15, wherein the handheld device includes the computing device, and wherein the emission-detecting device wirelessly communicates emissions data with the communication device.

18. The system of claim 15, wherein the emission-detecting device further comprises an air sampling device having a gas sampling tube fluidly coupled with the emission-detecting device so as to provide air to the emission-detecting device for sampling.

19. The system of claim 18, wherein the air sampling device comprises a rod configured to be grasped at a proximal end by a user, the gas sampling tube being coupled with a distal end of the rod so that a gas inlet port of the gas sampling tube is positioned near the distal end of the rod.

20. The system of claim 15, wherein the emission-detecting device comprises a flame ionization detection device and a metal hydride storage matrix for storing hydrogen gas for the flame ionization detection device.

21. A method for monitoring gas emissions within a geographic area comprising:
   providing a gas-monitoring device configured to be transported within the geographic area to monitor gas emissions, the gas monitoring device having a location detecting component and a emission-detecting component having a plurality of modes of operation;
   displaying a map of the geographic area on a display device;
   plotting, on the display device, a path within the geographic area along which the gas emissions device is to be transported, wherein the path is a path for walking;
   determining with the location detecting component, geographic locations of the gas-monitoring device within the geographic area as the gas-monitoring device is moved within the geographic area;
   with the emission-detecting component in a first mode of operation, measuring a quantity of one or more gases in the air for each geographic location as the gas-monitoring device is moved within the geographic area, wherein the first mode of operation is used along the path within the geographic area;
   with the emission-detecting component in a second mode of operation, obtaining enhanced measurements of the one or more gases in the air within one or more areas of concern within the geographic area, wherein the second mode of operation is used while diverting from the path within the geographic area;
   associating with a computing component of the gas-monitoring device, the geographic locations with the quantity of one or more gases so as to provide gas emissions data for each geographic location where measurements are taken; and
   communicating with a communication component of the gas-monitoring device, the gas emissions data to one or more external devices.

22. The method of claim 21, further comprising:
   calibrating the emission-detecting component of the gas-monitoring device comprising:
      determining that a reading of the emission-detecting component is within a defined tolerance when subjected to zero air; and
      determining that one or more of the following is within a defined tolerance when subjected to a calibration gas:
         an accuracy of the emission-detecting component;
         a precision of the emission-detecting component; or
         a response time of the emission-detecting component.

23. The method of claim 21, further comprising:
   determining one or more background air sampling conditions of the geographic area, the background air sampling conditions comprising either or both an upwind condition or a downwind condition;
   storing the one or more background air sampling conditions of the geographic area on a storage medium of the gas monitoring device; and
   communicating the one or more background air sampling conditions with the gas emissions data to the external device.

24. The method of claim 21, wherein the path along which the gas emissions device is to be transported is received from an external device.

25. The method of claim 21, further comprising alerting a user when the quantity of the one or more gases in the air exceeds a defined amount.

26. The method of claim 21, further comprising storing a first set of gas emissions data for the data measured with the emission-detecting component in the first mode of operation and storing a second set of gas emissions data separate from the first set of emissions data for the data measured with the emission-detecting component in the second mode of operation.

27. The method of claim 21, wherein communicating the gas emissions data to one or more external devices comprises transmitting the gas emissions data to an owner of the geographic area.

28. The method of claim 21, wherein the gas-monitoring device activates the measuring a quantity of one or more gases process by determining:
- that the gas-monitoring device is located at a defined gas monitoring position;
- that the gas-monitoring device has crossed a defined boundary of a trajectory along which the gas-monitoring device is moved.

29. The method of claim 21, further comprising moving the gas-monitoring device along the path within the geographic area, wherein:
- the path corresponds to a buried gas pipeline, or
- the geographic area corresponds to a landfill.

30. The method of claim 21, wherein:
- the first mode of operation collects samples at a first rate;
- the second mode of operation collects samples at a second rate; and
- the first rate is different from the second rate.

* * * * *